United States Patent
Yodh et al.

(10) Patent No.: US 6,304,771 B1
(45) Date of Patent: Oct. 16, 2001

(54) SYSTEMS AND METHODS FOR IMAGING FLUOROPHORES

(75) Inventors: Arjun G. Yodh, Merion; Britton Chance, Philadelphia, both of PA (US); David A. Boas, Newmarket, NH (US); Maureen O'Leary, Philadelphia, PA (US); Xingde Li, Cambridge, MA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 08/783,682

(22) Filed: Jan. 15, 1997

Related U.S. Application Data

(63) Continuation-in-part of application No. 08/637,645, filed as application No. PCT/US94/12486 on Oct. 31, 1994, now Pat. No. 5,917,190.

(51) Int. Cl.[7] .................................................. A61B 6/00
(52) U.S. Cl. ...................... 600/476; 250/458.1; 356/318
(58) Field of Search ................................ 600/476, 477, 600/309, 310; 356/39, 319, 346, 432, 436, 441, 442, 446, 239, 318; 250/358.1, 574, 575, 458.1, 459.1

(56) References Cited

U.S. PATENT DOCUMENTS

| | | | |
|---|---|---|---|
| 4,768,513 | * | 9/1988 | Suzuki .................................. 600/310 |
| 5,408,996 | * | 4/1995 | Salb ..................................... 600/310 |
| 5,413,108 | * | 5/1995 | Alfano .................................. 600/476 |
| 5,416,582 | * | 5/1995 | Knutson et al. ..................... 356/349 |
| 5,419,323 | * | 5/1995 | Kittrell et al. ....................... 600/407 |
| 5,421,337 | * | 6/1995 | Richards-Kortum et al. ........ 600/476 |
| 5,467,767 | * | 11/1995 | Alfano et al. ........................ 600/476 |
| 5,590,660 | * | 1/1997 | MacAulay et al. .................. 600/473 |
| 5,628,310 | * | 5/1997 | Rao et al. ............................ 600/310 |
| 5,772,580 | * | 6/1998 | Utsui et al. .......................... 600/160 |
| 5,784,157 | * | 7/1998 | Gorfinkel et al. ................... 356/318 |
| 5,865,754 | * | 2/1999 | Sevick-Muraca et al. .......... 600/476 |
| 5,917,190 | * | 6/1999 | Yodh et al. ....................... 250/458.1 |

OTHER PUBLICATIONS

S. John, Localization of light, *Physics Today*, vol. 44., pp. 32–40, (1991).

S. Feng, et al., Mesoscopic conductors and correlations in laser speckle patterns, *Science*, vol. 251, pp. 633–639, (1991).

D.J. Durian et al. Multiple light–scattering probes of foam structure and dynamics, *Science*, vol. 252, pp. 686–688. (1991).

B.J. Tromberg et al., Optical property measurements in turbid media using frequency domain photon migration, *SPIE, Future Trends in Biomedical Applications of Lasers*, vol. 1525, 52–58 (1991).

(List continued on next page.)

Primary Examiner—Brian L. Casler
(74) Attorney, Agent, or Firm—Woodcock Washburn Kurtz Mackiewicz & Norris LLP

(57) ABSTRACT

The systems comprise source means for illuminating the fluorophores with diffuse photon density waves of a first specified wavelength, whereby the fluorophores will fluoresce re-radiated diffuse photon density waves of a second wavelength after being illuminated with the diffuse photon density waves of the first specified wavelength; detection means for detecting the re-radiated diffuse photon density waves of the second wavelength, wherein there is a phase shift between the diffuse photon density waves of the first wavelength and the diffuse photon density waves of the second wavelength; and processing means interfaced with the detection means for processing data corresponding to the phase shift and the amplitude of the re-radiated waves to determine concentration and lifetime of the fluorophores as a function of spatial position of the fluorophores in the turbid medium.

16 Claims, 21 Drawing Sheets

OTHER PUBLICATIONS

M.Maris et al. Frequency domain measurements of changes of optical pathlength during spreading depression in a rodent brain model, *SPIE, Time–Resolved Spectroscopy and Imaging of Tissues*, vol. 1431, pp. 136–148 (1991).

F. W. Flickinger et al. Differentiation of benign from malignant breast masses by dynamic time–intensity evaluation of contrast enhanced MRI, *Proceedings of the Society of Magnetic Resonance in Medicine, Eleventh Annual Scientific Meeting*, Berlin, Germany (1992).

J.B. Fishkin et al., Propagation of photon–density waves in strongly scattering media containing an absorbing semi–infinite plane bounded by a straight edge, *Journal of the Optical Society of America*, vol. A 10, pp. 127–140 (1993).

J.M. Schmitt et al., Interference of diffusive light waves, *Journal of the Optical Society of America*, vol. A 9 pp. 1832–1843 (1992).

B. Chance et al. Highly sensitive object location in tissue models with linear in–phase and anti–phase multi–element optical arrays in one and two dimensions, *Proceedings of the National Academy of Sciences USA*, vol. 90, pp. 3423–3427.

Lakawicz, J.R., "Principles of Fluorescence Spectroscopy," *Plenum New York*, 1983, pp. 258–266.

Milonni and Eberly, "Lasers," *Wiley, New York*, 1988, pp. 218–222.

Rumsey, William L. et al., "Imaging of Phosphorescence: A Novel Method for Measuring Oxygen Distribution in Perfused Tissue," Sep. 23, 1988.

Lakowicz, J.R., et al, "Fluorescence Lifetime Imaging of Calcium Using Quin–2," Cell Calcium, 1992, 13, pp. 131–147.

O'Leary, M.A. et al., "Refraction of Diffuse Photon Density Waves," Nov. 2, 1992, vol. 69, No. 18.

Cubeddu, R, et al., "Time–Gated Fluorescence Imaging for the Diagnosis of Tumors in a Murine Model," *Photochemistry and Photobiology*, 1993, vol. 57, No. 3, pp. 480–485.

Szmacinski, Henryk, et al., "Optical Measurements of pH Using Fluroescence Lifetimes and Phase–Modulation Fluorometry," *Anal. Chem.*, 1993, 65, pp. 1668–1674.

Fishkin, Joshua B. et al., "Propagation of Photon–Density Waves in Strongly Scattering Media Containing an Absorbing Semi–Infinite Plane Bounded by a Straight Edge," *Optical Society of America*, Jan. 1993, vol. 10, No. 1.

Knuttel, A. et al., "Acousto–Optic Scanning and Interfering Photon Density Waves for Precise Localization of an Absorbing (or Fluorescent) Body in a Turbid Medium," *Rev. Sc. Instrum.*, Mar. 1993.

Boas, D.A., et al., "Scattering and Wavelength Transduction of Diffuse Photon Density Waves," *Physical Review E*, May, 1993, vol. 47, No. 5.

Wu, Jun, et al., "Analytical Model for Extracting Intrinsic Fluorescence in Turbid Media," *Applied Optics*, Jul. 1, 1993, vol. 32, No. 19.

O'Leary, M.A. , "Reradiation and Imaging of Diffuse Photon Density Waves Using Fluorescent Inhomogeneities," *Journal of Luminescence* 60 & 61, 1994, pp. 281–286.

Durkin, A.J. et al., "Relation Between Fluorescence Spectra of Dilute and Turbid Samples," *Applied Optics*, Jan. 20, 1994, vol. 33, No. 3.

Patterson, Michael S. et al., "Mathematical Model for Time–Resolved and Frequency–Domain Fluorescence Spectroscopy in Biological Tissues," *Applied Optics*, Apr. 1, 1994, vol. 33, No. 10.

Boas, D.A. et al., "Scattering of Diffuse Photon Density Waves by Spherical Inhomogeneities within Turbid Media: Analytic Solution and Applications," *Proc. Natl. Acad. Sci. USA*. May 1994, vol. 91, pp. 4887–4891.

Haskell, Richard C. et al., "Boundary Conditions for the Diffusion Equation in Radiative Transfer," *Optical Society of America*, Oct. 1994, vol. 11, No. 10.

Sevick–Muraca, Eva M., et al., "Origin of Phosphorescence Signals Reemitted from Tissues," *Optical Society of America*, 1994, vol. 19, No. 23.

Chance, Britton, et al., "Progress in Biomedical Optics –Proceedings of Optical Tomography, Photon Migration, and Spectroscopy of Tissue and Model Media: Theory, Human Studies, and Instrumention," *The International Society for Optical Engineering* Feb. 5–7, 1995, vol. 2389, Part Two of Two Parts.

Yodh, Arjun, et al., "Spectroscopy and Imaging with Diffusing Light," *Physics Today*, Mar. 1995.

O'Leary, M.A. et al., "Experimental Images of Hetergeneous Turbid Media by Frequency–Domain Diffusing–Photon Tomography," *Optical Society of America*, Mar. 1, 1995.

Hutchinson, Christina L. et al., "Fluorescence Lifetime––Based Sensing in Tissues: A Computational Study," *Biophysical Journal*, Apr. 1995, vol. 68, pp. 1574–1582.

Aronson, Raphael, "Boundary Conditions for Diffusion of Light," *Optical Society of America*, Nov. 1995, vol. 12, No. 11.

O'Leary, M.A. et al., "Fluorescence Lifetime Imaging in Turbid Media," *Optics Letters*, Jan. 15, 1996, vol. 21, No. 2.

Li, X.D. et al., "Fluorescent Diffuse Photon Density Waves in Homogeneous and Hetergeneous Turbid Media: Analytic Solutions and Applications," *Applied Optics*, Jul. 1, 1996, vol. 35, No. 19.

Yoo, K.M. et al., "Imaging through a scattering wall using absorption," *Optic Letters*, 1991, vol. 16, No. 14, p. 1068.

Benaron, David A., et al., "Optical Time–of–Flight and Absorbance Imaging of Biologic Media," *Science*, 1993, vol. 259, p. 1463.

Piston, David W., et al., "Two–photon–excitation flourescence imaging of three–dimensional calcium–ion activity," *Applied Optics*, 1994, vol. 33, No. 4, p. 662.

Tromberg, Bruce J. et al., "Frequency–Domain Photon Migration in Turbid Media," *Optical Society of America Proceedings*, 1994, vol. 21.

Folkman, Judah, "The Role of Angiogenesis in Tumor Growth," *Academic Press, Ltd.*, 1992, vol. 3, pp. 65–71.

Bambot, Shabbir B., et al., "Potential Applications of Lifetime–based, Phase–Modulation Fluorimetry in Bioprocess and Clinical Monitoring," *Trends, Biotech.*, 1995, vol. 13, pp. 106–115.

Vaupel, Peter W. et al., "Hetergeneous Oxygen Partial Pressure and pH Distribution in C3H Mouse Mammary Adenocarcinoma," *Cancer Research*, May, 1981, vol. 41, pp. 2008–2013.

Kak, Avinash, C., et al., "Principles of Computerized Tomographic Imaging," *IEEE Press*, New York, 1998, Chap. 6, p. 211.

Patterson, Michael S., et al., "Time Resolved Reflectance and Transmittance for the Non–Invasive Measurement of Tissue Optical Properties," *Applied Optics*, 1989, vol. 28, No. 12.

Wu, Jun. et al., "Time–Resolved Mutichannel Imaging of Fluorescent Objects Embedded in Turbid Media," *Optical Society of America*, 1995, vol. 20, No. 5.

Li, Xingde, et al., "Tumor Localization Using Fluorescence of Indocyanine Green (ICG) In Rat Models," *The Society of Photo–Optical Instrumentation Engineers*, 1995, vol. 2389, Part Two.

Valduga, Giuliana, et al., "Steady State and Time–Resolved Spectroscopic Studies on Zinc(II) Phthalocyanine in Liposomes", 1992, vol. 16, pp. 331–340.

Madsen, Steen J., et al., "Numerical Modelling and Experimental Studies of Light Pulse Propagation in Inhomogeneous Random Media," *The Society of Photo–Optical Instrumentation Engineers*, 1993, vol. 1888.

Hutchinson Christina L., et al., "Fluorescence–Lifetime Spectroscopy and Imaging in Random Media" *The Society of Photo–Optical Instrumentation Engineers*, 1995, vol. 2389, Part One.

* cited by examiner

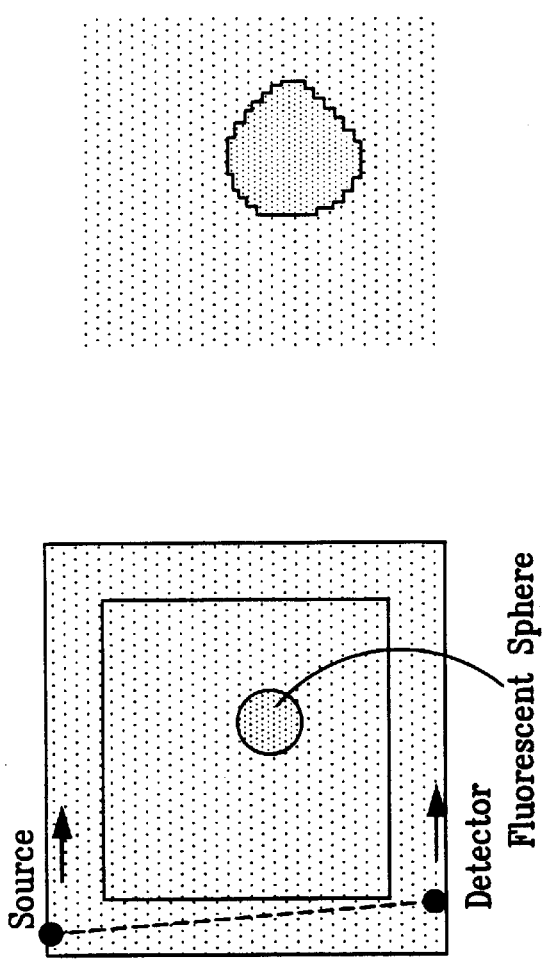
*FIG. 16A*
*FIG. 16B*
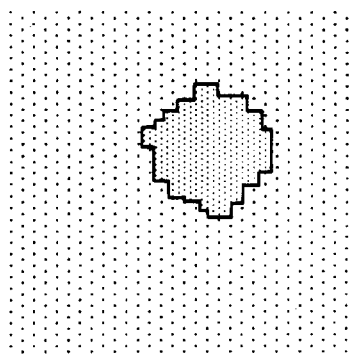
*FIG. 16D*
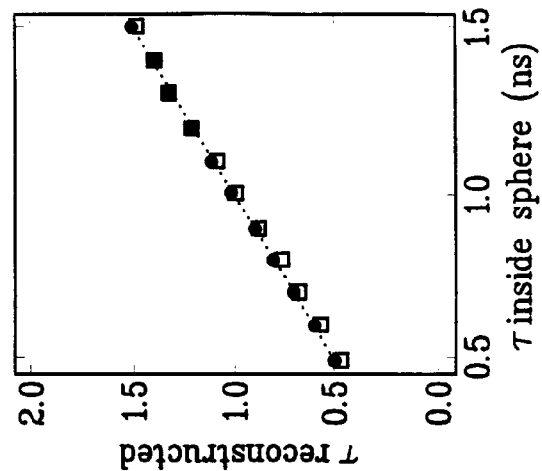
*FIG. 16E*
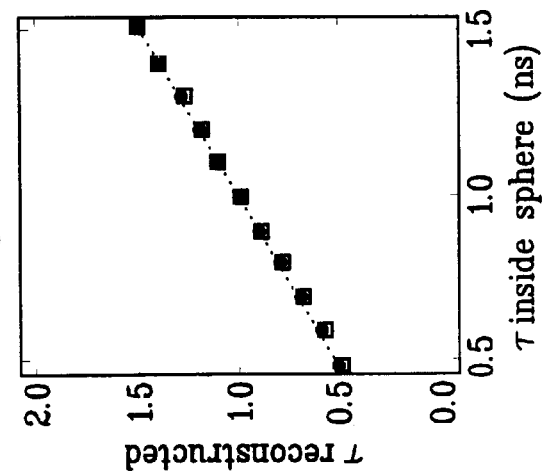
*FIG. 16C*

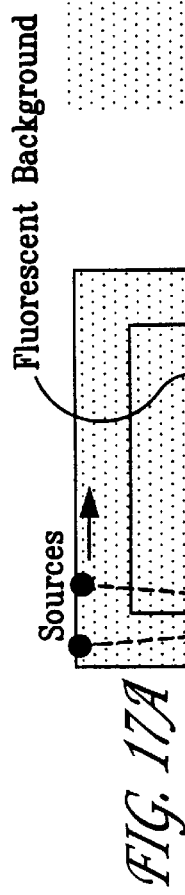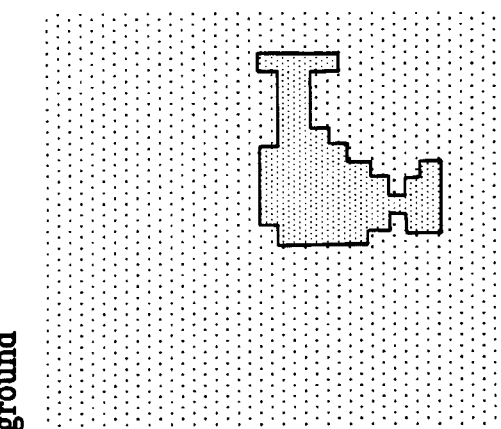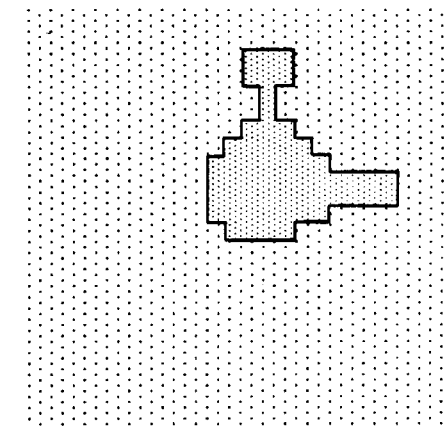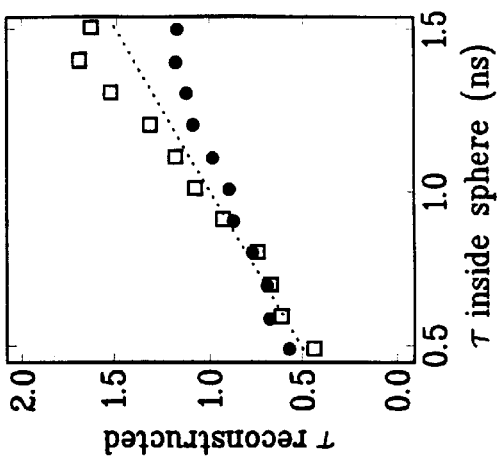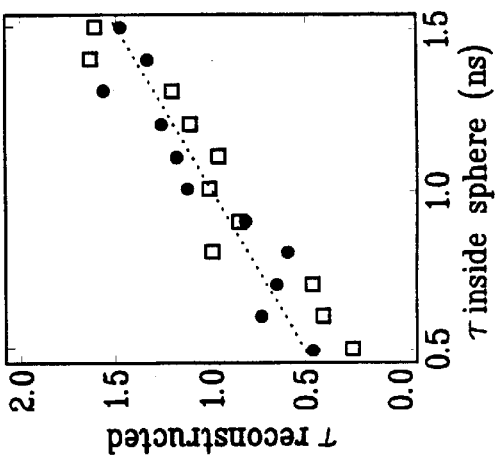
FIG. 17A
FIG. 17B
FIG. 17C
FIG. 17D
FIG. 17E

SYSTEMS AND METHODS FOR IMAGING FLUOROPHORES

RELATED APPLICATIONS

This application is a continuation-in-part of U.S. application Ser. No. 08/637,645, filed Jul. 25, 1996, issued Jun. 29, 1999 as U.S. Pat. No. 5,917,190, which was the National Stage of International Application No. PCT/US94/12486, filed Oct. 31, 1994, which claims priority from U.S. application Ser. No. 08/145,466, filed Oct. 29, 1993.

FIELD OF THE INVENTION

This invention relates generally to imaging of objects. More specifically, this invention relates to methods and apparatus for imaging objects using diffuse light.

BACKGROUND OF THE INVENTION

Techniques for imaging objects have been used for nearly a century in the medical arts for diagnosing and understanding the myriad diseases and maladies that afflict the human body. Imaging techniques have also found use in such diverse fields as radio astronomy, sonar, radar and other fields which require information about an object which is not readily visible to the naked eye and therefore not easily examined. Medical imaging techniques include, for example, X-ray imaging, positron emission tomography (PET), ultrasound imaging and the well known magnetic resonance imaging (MRI).

In all of the imaging techniques mentioned above, narrow band frequency radiation illuminates the object of interest to produce reflected or emitted radiation which is then gathered from the object by a detector. The reflected or emitted radiation is then processed by an imaging algorithm to obtain useful information about the object.

In medical applications, the use of ionizing radiation in imaging, for example with X-rays, involves significant health risks to a patient when the patient is exposed to the radiation for prolonged periods of time or in multiple imaging schemes. Furthermore, certain of these imaging techniques undesirably involve the use of invasive procedures which are both costly and painful. Yet other techniques such as MRI do not yield consistently useful clinical results.

There has thus arisen in the medical imaging art an interest in developing non-invasive, safe and relatively fast techniques which can take advantage of the natural scattering of visible and infrared light through media containing objects to be imaged. Techniques using diffuse light could be used in conjunction with other imaging schemes such as X-ray imaging or MRI to produce highly useful clinical images for diagnostic purposes.

Much of the progress in imaging with diffusive light has focused on ballistic techniques using lasers. With these techniques, an intense pulsed laser illuminates a sample. By time gating photons that have been scattered only a few times and rejecting all other photons, the optical absorption of the medium and objects found therein can be mapped. This technique works best when the allowed time window is short and the photons deviate the least from their "ballistic" trajectory. Unfortunately, the transmittal intensity of unscattered photons diminishes exponentially with increasing sample thickness.

Because of the limitations of ballistic imaging, it is difficult to obtain high quality images of relatively thick objects with low power lasers. Examples of ballistic imaging techniques are disclosed in K. M. Yoo, F. Lie and R. R. Alfano, *Optics Letters*, Vol. 16, p. 1068 (1991), and in D. A. Benaron and D. K. Stevenson, *Science*, Vol. 259, p. 1463 (1993).

A second technique for imaging using diffuse light is optical phase modulation. Phase modulation techniques have permitted the location of single absorbers using low power, continuous wavelength lasers. In accordance with these techniques, an amplitude modulated source creates photon density waves that acquire anomalous phase shifts due to the absorber. For the case of a single absorber, the distortions are readily interpreted; however for a more complicated object a general analysis is required.

An example of imaging with diffuse light is disclosed in U.S. Pat. No. 5,119,815, Chance where scattered light was applied to a biological imaging application. The Chance patent discloses a technique for solving the diffusion equation for a homogeneous medium to obtain the overall optical absorption characteristics. This was possible for the homogeneous medium because the long time limit of the logarithmic derivative of the detected intensity yields the absorption characteristics directly. Thus the absorption characteristics for uniform structures may be obtained with the methods and apparatus disclosed in the Chance patent.

Still other attempts to image with diffuse light are disclosed in U.S. Pat. No. 5,070,455, Singer et al. In the Singer et al. system, light intensities are measured at many sensor positions (pixels), initial values of absorption or scattering coefficients are assigned at each pixel, and then a new set of intensities at each pixel is calculated. The calculated intensities are compared to the real intensities, and the intensity differences are used to generate a subsequent interaction of absorption or scattering values for each pixel.

The methods described in Singer et al. usually require many iterations since the absorption or scattering values may not converge rapidly. Furthermore, the Singer et al. system utilizes cumbersome Monte-Carlo statistical techniques which consume large amounts of processing time without guaranteeing computational success. Singer et al.'s methods may also produce false local minima providing misleading results for the absorption characteristics.

Thus prior imaging techniques using diffuse light for scattering fail to solve a long-felt need in the art for robust imaging techniques which can produce reliable images in biological systems. Solution of the aforementioned problems has heretofore eluded the medical imaging art.

SUMMARY OF THE INVENTION

The aforementioned deficiencies in the imaging art are overcome by methods and apparatus provided in accordance with the present invention which provide imaging of objects in turbid media using diffuse light.

In a preferred embodiment of the invention an imaging system comprises an illumination source that generates oscillatory diffuse photon density waves to illuminate the object, a detector for detecting diffuse photon density waves produced as a result of the diffuse photon density waves interacting with the object, and a processor interfaced with the detector for processing data corresponding to the photon density waves detected by the detector to determine at least a position of the object. The turbid medium and the object have associated therewith at least one diffusion coefficient and the diffuse photon density waves which illuminate the object diffract around or refract through the object as a result of their interaction with it, thereby producing a distorted wavefront such that after the detector means detects the distorted wavefront the processor determines the diffusion coefficient of the turbid medium and the object. More preferably, the processor constructs phase and amplitude contours corresponding to propagation of the distorted wavefront and further determines at least the position of the object from the phase and amplitude contours, thereby imaging the object.

In yet a further preferred embodiment of imaging systems provided in accordance with the invention, a display are interfaced with the processor for displaying the image of the object, the illumination comprises at least one laser, and the detector comprises an optical fiber interfaced with a photomultiplier tube.

Further aspects of the invention provide imaging of a fluorescent object such that the diffuse photon density waves having a first wavelength cause the object to fluoresce, thereby producing re-radiated diffuse photon density waves having a second wavelength such that after the detector detects the re-radiated diffuse photon density waves, the processor can image the object.

In the embodiment of the invention where fluorescent, re-radiated diffuse photon density waves are detected, the illumination source preferably comprises a plurality of lasers oriented around the object which alternately irradiate the object with the diffuse photon density waves of the first wavelength to cause the object to fluoresce. The detector comprises an optical fiber that is placed in proximity to the object and a photomultiplier tube interfaced to the optical fiber. The imaging system further comprises switch means interfaced with each of the plurality of lasers for alternately and sequentially turning on and off each laser, and radio frequency driving means interfaced through the switch means with the lasers for driving the lasers to produce the diffuse photon density waves of the first wavelength.

Alternatively, the imaging system comprises a plurality of lasers each having a spatial location with respect to the object. Each laser is more preferably modulated at all times during imaging at a different frequency in a frequency range around a specified frequency, thereby producing a power spectrum associated with each spatial location around the object. Analysis means are provided interfaced with the detector and the processor for analyzing the power spectrums associated with each spatial location to determine the position of the object.

In still a further preferred embodiment of imaging systems which take advantage of fluorescent, re-radiated diffuse photon density waves, the source means comprises a phased-array. The phased-array, preferably comprises at least two lasers that are substantially one hundred and eighty degrees out of phase with each other, thereby producing the diffuse photon density waves having the first wavelength which interfere destructively to produce an amplitude null line and a substantially one hundred and eighty degree phase shift across the null line equidistant from the lasers. By scanning the null line with the phased-array the processor can produce an image of the object in the turbid medium.

Systems and methods provided in accordance with the present invention will provide efficient imaging of tumors and other maladies that effect human tissue. These systems will also prove to be much more economical to build when compared to prior imaging systems, since they will not require the complex machinery that is associated with prior imaging systems such as MRI. Furthermore, since the methods and apparatus provided in accordance with the present invention utilize diffuse light for imaging, more reliable images of tumors will be presented to the medical diagnostician or clinician so that cancerous tumors and other inhomogeneities in the tissue will be detected earlier and more readily. This holds the promise of saving lives and reducing the overall costs of medical care.

Systems for imaging fluorophores in a turbid medium also satisfy the above long-felt needs. Preferably, the systems comprise an illumination source for illuminating the fluorophores with diffuse photon density waves of a first specified wavelength, whereby the fluorophores will fluoresce re-radiated diffuse photon density waves of a second wavelength after being illuminated with the diffuse photon density wavelengths of the first specified wavelength. The systems further comprise a detector for detecting the re-radiated diffuse photon density waves of the second wavelength, wherein there is a phase shift between the diffuse photon density waves of the first wavelength and the diffuse photon density waves of the second wavelength. Even more preferably, processor are interfaced with the detection for processing data corresponding to the phase shift and the amplitude of the re-radiated waves to determine concentration and lifetime of the fluorophores as a function of spatial position of the fluorophores in the turbid medium.

The features, objects and advantages of the invention will be understood by those with skill in the art from the following detailed description of the preferred embodiments thereof when read in conjunction with the drawings which are first described briefly below.

BRIEF DESCRIPTION OF THE DRAWINGS

FIGS. 16A through 16E show scanning geometry versus varied actual lifetime of the fluorophores without background fluorescence.

FIGS. 17A through 17E show scanning geometry versus varied actual lifetime of the fluorophores with background fluorescence.

DETAILED DESCRIPTION OF PREFERRED EMBODIMENTS

Figure 1:
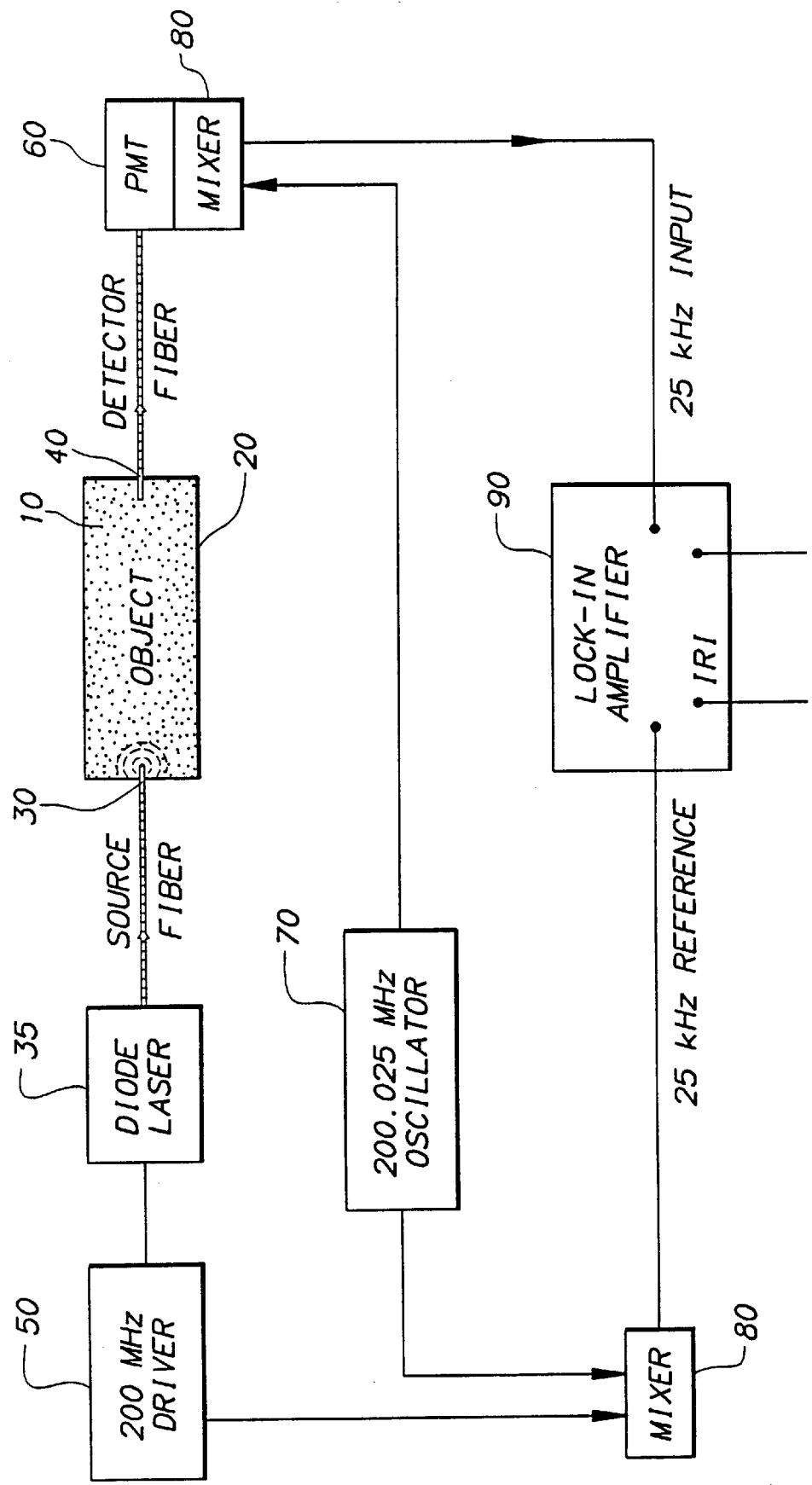
FIG. 1 is a schematic representation of an imaging system using diffuse light wherein scattering experiments with diffuse photon density waves occurs.

Propagating disturbances are produced in a dense, turbid medium containing objects when amplitude modulated light sources are introduced into the turbid medium. In biological and medical imaging applications, human tissue, such as breast tissue containing tumors, is such a turbid medium containing objects to be imaged. In accordance with the present invention, an oscillatory light source introduces diffuse photon density waves (hereinafter referred to as "DPDW") in the turbid medium. While the results described herein have been achieved with respect to several experimental apparatus to be described hereafter, those with skill in the art will immediately recognize that the techniques and apparatus disclosed are readily applicable to imaging human body tissue which is infected with tumors or other maladies that will appear as inhomogeneities in the tissue which is a turbid medium.

The inventors of the subject matter herein claimed and disclosed have discovered that DPDW can be used in at least two ways to perform imaging. In a first preferred embodiment, DPDW are introduced into a turbid medium and refracted through and diffracted around objects in the medium, thereby producing a distorted wavefront which can then be analyzed to yield useful information concerning at least a position and size of the object around which the DPDW have been refracted.

In a further preferred embodiment, the inventors have determined that by introducing fluorescence to the object, photons in the re-radiated DPDW will be emitted from the object at a shifted wavelength with respect to the original DPDW and the re-radiated DPDW then analyzed to determine at least the position of the fluorescent objects in the turbid medium. This is particularly useful for imaging of tumors since in prior, non-diffuse light imaging techniques fluorescent dyes which respond to various forms of radiation have typically been introduced into tumors, thereby yielding information about the location and size and nature of the tumor under examination.

Thus, imaging tumors and objects in turbid media with diffuse light will in the future produce significant and effective images for diagnostic and clinical purposes.

I. The Basic Theory of DPDW Propagation in a Turbid Medium

The basic mechanics of wave propagation in a turbid medium have been explored by the inventors when performing imaging in accordance with the present invention. DPDW are scalar, over-damped, traveling waves of light energy density, denoted U(r,t). They propagate through any medium in which the transport of light energy density, U, is governed by the "diffusion equation," which is $$\frac{\partial U}{\partial t} = D \nabla^2 U$$

where D is the "diffusion coefficient" for the medium. This diffusion equation holds for a non-absorbing medium. Some examples of optically turbid media include dense suspensions of micrometer-sized spheres, human tissue, paints, foams, and Intralipid (a mixture of water, soybean oil and egg yolk). The introduction of amplitude modulated light into a turbid medium produces a macroscopic ripple of brightness that is microscopically composed of individual photons undergoing random walks. The disturbances arise whenever the diffusive system is driven by an oscillating source.

The oscillatory part of the solution for an infinite, non-absorbent, homogeneous turbid medium in the presence of a point source located at the origin follows the form:

$$U(r,t) = (A/Dr) (\exp\{-kr\}) (\exp\{i(kr-\omega t)\})$$

where A is a constant, r is the radial distance from the origin, D is the diffusion coefficient for light in the medium, ω is the source modulation frequency, and $k = (\omega/2D)^{1/2}$. Although the wave is very rapidly attenuated, it has a well-defined wavelength, amplitude and phase at all points. Interestingly, the wavelength can be altered by modifying D or ω.

When absorption is present, a similar solution to Equation (1) can be obtained, but the real and imaginary parts of the wave vector k are different and depend explicitly on the sample absorption length (as well as the photon random walk step for inverse scattering factor). The macroscopic disturbance obeys a Helmholtz equation, and therefore has many properties that are normally associated with conventional electromagnetic radiation. Thus, DPDW display refraction, diffraction, and interference properties similar to those observed with conventional electromagnetic radiation propagating through media. By examining the energy contours produced as a result of the interaction of the DPDW with the objects in the medium according to the techniques of the present invention, the objects can be imaged to obtain useful clinical data.

II. Imaging Using Refracted DPDW

In a preferred embodiment, an apparatus for imaging objects in a turbid medium is shown schematically in FIG. 1. The object 10 may contain smaller objects such as tumors which must be characterized for clinical purposes. For experimental purposes, the dense turbid medium imaged is Intralipid, a polydisperse suspension of particles having an average diameter of ~0.4 μm, but a relatively wide range of sizes (i.e., from ~0.1 to ~1.1 μm). By changing the solution concentration of the Intralipid, it is possible to vary the light diffusion coefficient, D, of the medium. The photon transport mean free path l* was about 0.2 cm in a 0.5% concentrated solution.

To perform imaging of the smaller objects in the Intralipid, a large fish tank 20 (30 cm×30 cm×60 cm) is filled with this material. When the absorption is very small, the suspensions in the Intralipid are dilute, and therefore the diffusion coefficient is inversely proportional to the Intralipid concentration.

In a preferred embodiment, a source fiber 30 and detector fiber 40 (both ~4 mm in diameter) are placed in proximity to object 10. The source light 30 is preferably derived from a 3-mW diode laser 35 operating at about 816 nm. The diode laser 35 is amplitude modulated at 200 MHz by driver 50, and the position of the source fiber 30 is fixed. The detector fiber 40 is in detecting proximity to the object 10 and is further connected to a photomultiplier tube 60 on its other end. In order to facilitate phase and amplitude measurements, both the reference from the driver 50 and the detected signal are down-converted to 25 kHz by heterodyning with a second oscillator 70 to 200.025 MHz. Mixers 80 preferably combine the frequencies to produce the 25 kHz signals shown. The low-frequency signals are then measured using a lock-in amplifier 90.

In a more preferred embodiment, the phase shift (and ac amplitude) of the detected light is measured with respect to the source 30 at each point on a 0.5-cm square planar grid throughout the sample. Constant phase contours are then determined by linear interpolation of the grid data. The sensitivity of the apparatus shown in FIG. 1 is about $10^5$. Since the signal amplitude decays by $>e^{-2\pi}$ in one wavelength, the range of the apparatus is limited to slightly more than one wavelength. Nevertheless, it is possible to clearly distinguish the essential physical phenomena of the DPDW scattering through the object 10 with this apparatus.

The results obtained by imaging with the system of FIG. 1 demonstrate that a "diffusional index of refraction" exists for DPDW, and that it is possible to manipulate the diffusional index of refraction by controlling the photon diffusion coefficients (D) of adjacent turbid media. This is of considerable importance in biological systems, where the natural curvature of organs such as the brain, heart, or kidney, together with changes of scattering and absorption as in the grey-white matter transition of the brain, can lead to significant modifications of the trajectories of diffuse photons.

Figure 2:
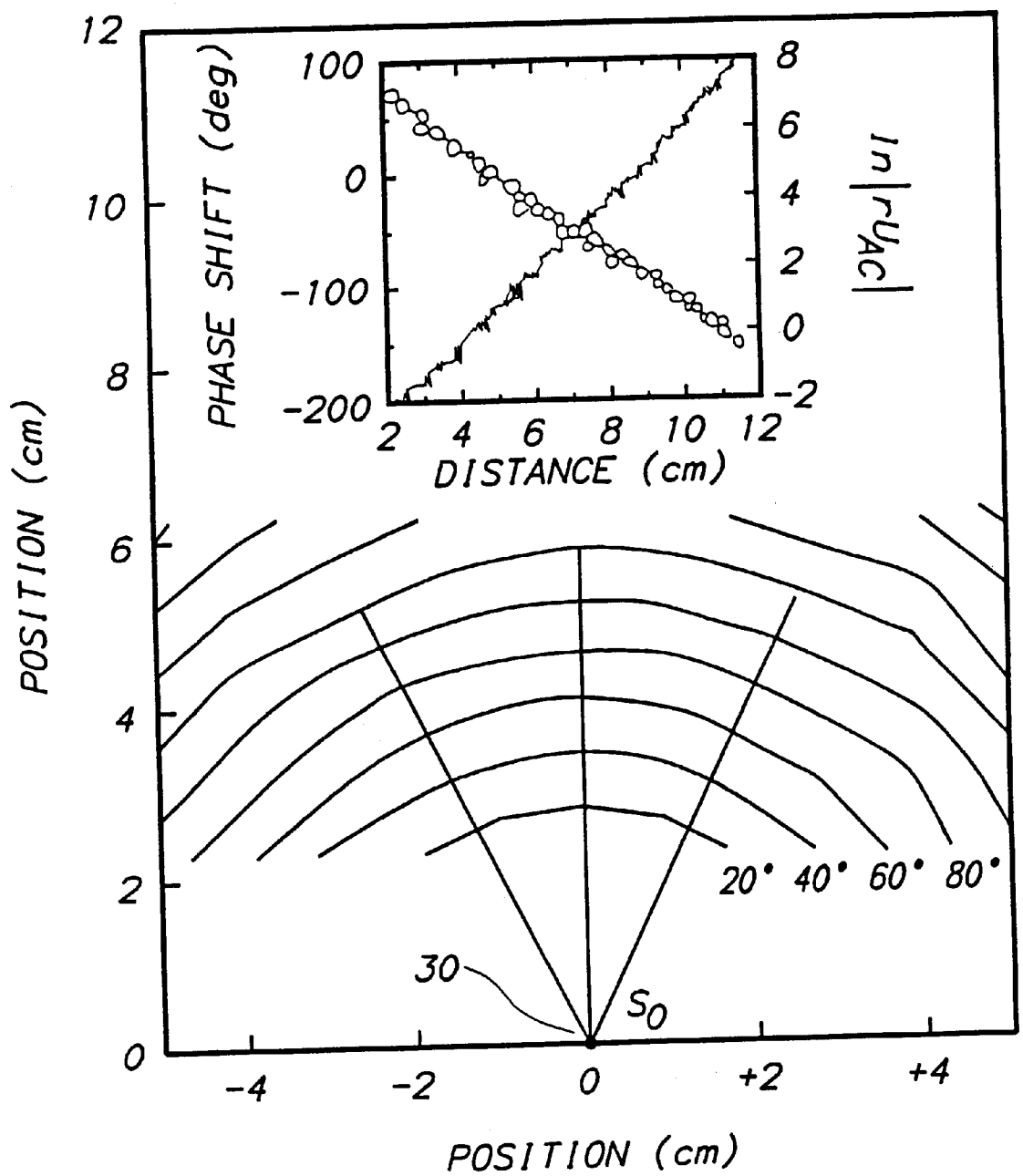
FIG. 2 depicts measured constant contours of diffuse photon density waves propagating through a turbid medium.

Results for a ~0.5% concentrated homogeneous turbid medium are illustrated in FIG. 2. Constant phase contours are shown at 20° intervals about the source. The contours are approximately circular, and their radii can therefore be extrapolated back to the source 30. In the insert of FIG. 2, the phase shift and the quantity $\ln|rU_{ac}(rt)|$ as a function of radial distance from the source are plotted. From these measurements it is possible to determine that the wavelength of the DPDW is 11.2 cm, the photon transport mean free path is ~0.2 cm, and the photon absorption length is ~52 cm in ~0.5% Intralipid at 22° C. In this case, the photon absorption can be attributed almost entirely to water.

Figure 3:
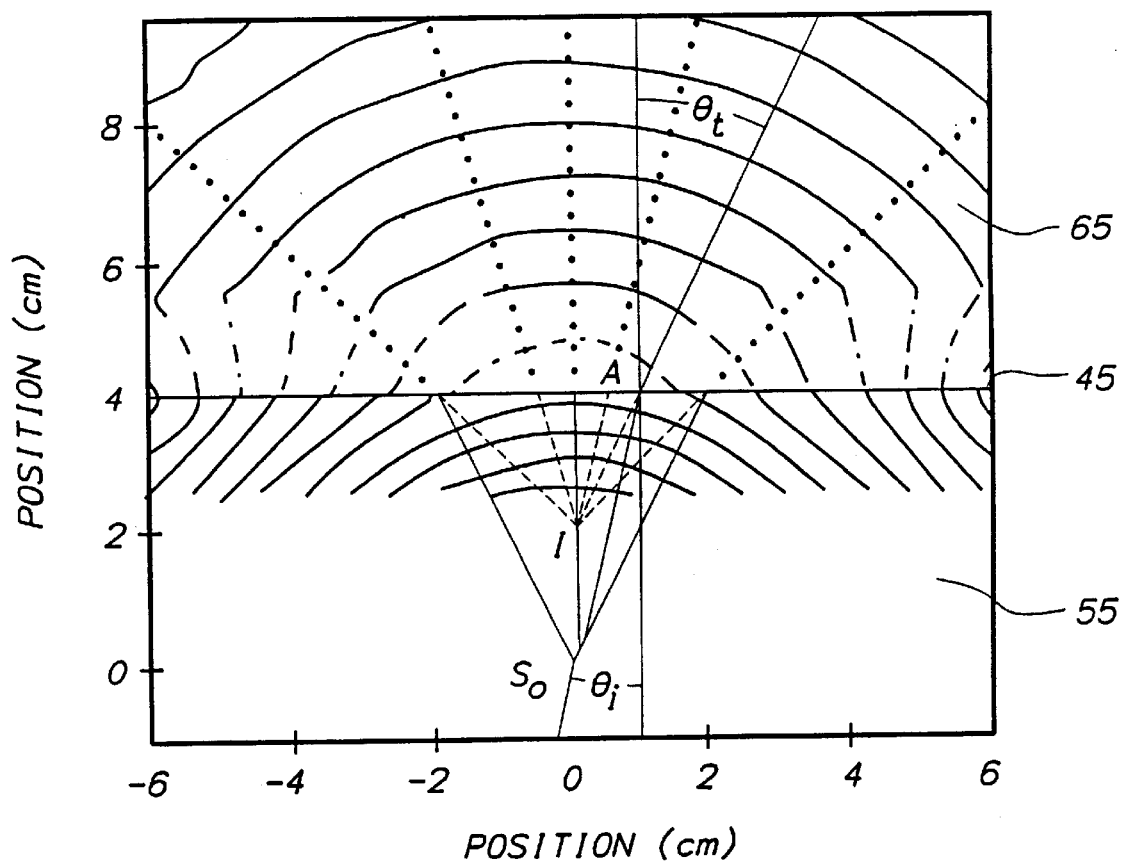
FIG. 3 depicts measured constant phase contours of diffuse photon density waves propagating through turbid media and refracting across a plane boundary between two turbid media with different light diffusion coefficients.
Figure 4:
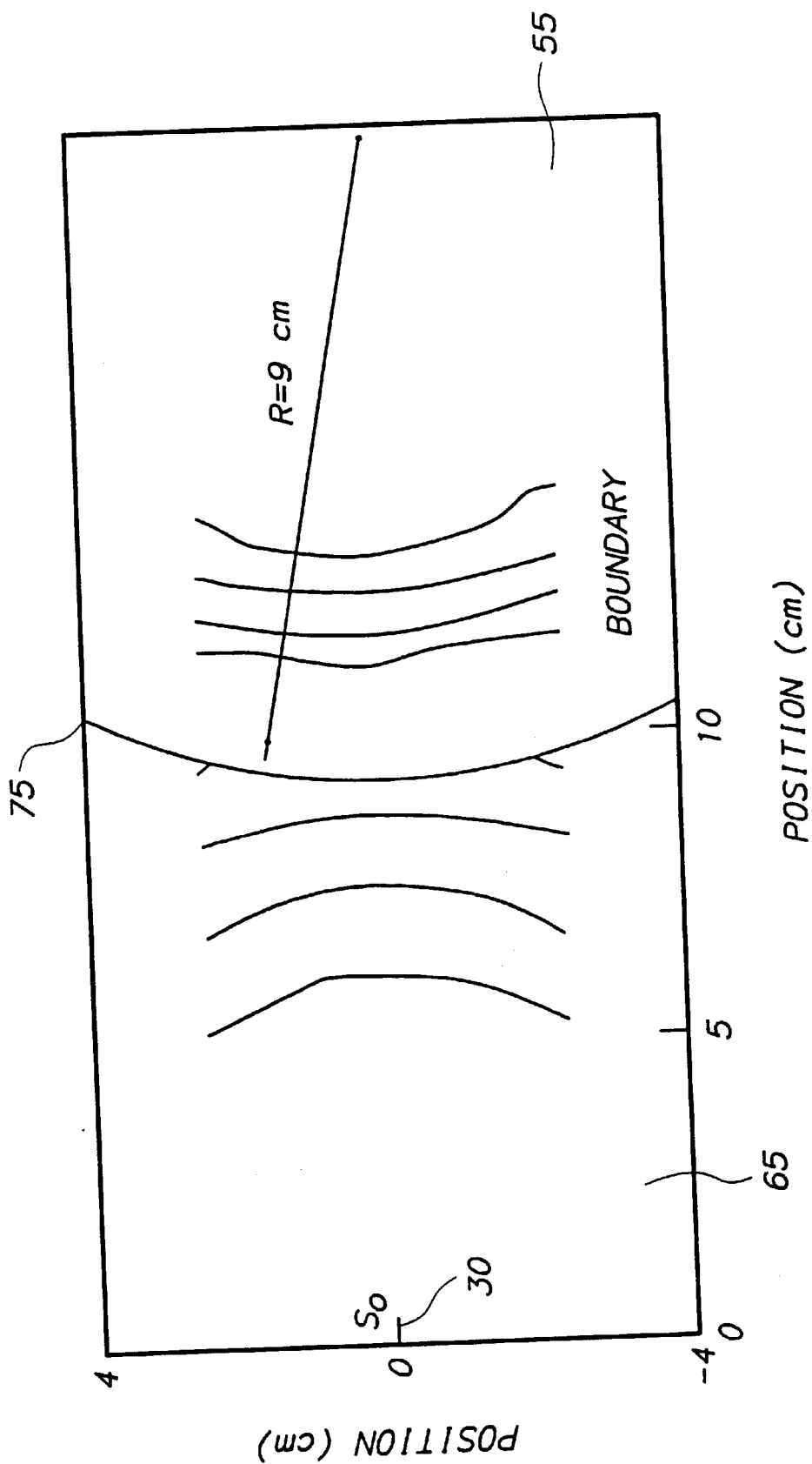
FIG. 4 is a graph of phase contours of diffuse photon density waves propagating through turbid media after refracting across a cylindrical boundary separating two turbid media wherein lensing effects are observed.

Referring to FIGS. 3 and 4, refraction of the DPDW is shown in three ways: (1) when a plane, acrylic partition or (2) a cylindrical acrylic partition is placed in the tank to simulate a boundary, and (3) when no partition is in place so that the medium is homogeneous. In FIG. 3, constant phase contours exist at about every 20°. When the plane boundary 45 is introduced, the lower medium 55 has a concentration, $c_l$, ~1.0% and light diffusion coefficient $D_l$. The upper medium 65 has a concentration, $c_u$, ≈0.25% and light diffusion coefficient $D_l$. The contours below boundary 45, shown at the 4 cm position on the y-axis, are just the homogeneous media contours without refraction. These contours are obtained before the partition is introduced. The contours above the boundary 45 are derived from the DPDW that are transmitted into the less concentrated medium.

Theory predicts that the wavelength in the less dense medium, $\lambda_u$, is 14.8 cm, and should be greater than the wavelength of the DPDW in the incident medium, $\lambda_l$, which is 8.17 cm. The ratio of the two wavelengths should equal the ratio of the diffusional indices of refraction of the two media. As is predicted, $\lambda_u = \lambda_l (D_l/D_u)^{-\frac{1}{2}} \sim \lambda_l(c_l/c_u)^{1/2}$.

Theory also predicts that the apparent source position $S_i$, as viewed from within the upper medium 65, should be shifted from the real source position, $S_o$=4.0±0.2 cm, by a factor $\lambda_l/\lambda_u$=0.55. This is verifiable from the data of FIG. 3 since, using the radii from the full contour plots, the apparent source position is shifted from 4.0±0.2 to 2.0±0.25 cm.

In accordance with the invention, FIG. 3 explicitly demonstrates Snell's law for DPDW. This can be seen by following the ray from $S_o$ to the point A at the boundary 45, and then into the upper medium 65. The ray in the lower medium 55 makes an angle $\theta_i$=14° with respect to the surface normal. The upper ray is constructed in the standard way between the apparent source position $S_i$, through the point A on boundary 45, and into the medium 65 above the boundary. The upper ray is perpendicular to the circular wave fronts in the less dense medium 55, and makes an angle $\theta_t$=26.6° with respect to the boundary normal. Therefore, it can be seen graphically that sin $\theta_i$/sin $\theta_t$=0.54≈$\lambda_l/\lambda_u$, so that Snell's law accurately describes the propagation of DPDW across boundary 45.

The inventors have also determined that by using a circular boundary (shown generally at 75 in FIG. 4) to separate the two turbid media, the curvature of the DPDW can be altered in analogy with a simple lens in optics. Referring to FIG. 4, two semi-infinite media are separated by curved boundary 75, and the medium 55 on the right is more concentrated. The constant phase contours of the transmitted wave exhibit a shorter wavelength, and are clearly converging toward some image point to the right of the boundary. The medium 65 on the left ($\lambda_l$) has an Intralipid concentration of ~0.1%, and the medium 55 on the right ($\lambda_r$) has a concentration of ~1.6%.

The wavelength ratio is measured to be $\lambda_r/\lambda_l$=3.8±0.3. The curved surface 75 has a radius R=9.0±0.4 cm. The position of source 30 is $S_o$=9.4±0.3 cm. The image position is determined to be $S_i$=12±2 cm. This result deviates somewhat from the well-known paraxial result from geometrical optics for imaging by a spherical refracting surface. The deviation is primarily a result of spherical aberration. However, in accordance with the invention, the curvature of the wave fronts is reversed after traversing the circular boundary 75.

The results shown in FIGS. 2, 3 and 4 which are obtained from the apparatus of FIG. 1 show that it is possible to exert substantial control over the transport of diffuse light in dense random media. The inventors have clearly demonstrated that the index of refraction of DPDW in such a medium depends on the photon diffusion coefficient or random walk step of the photons in the medium. This allows imaging of inhomogeneities in the medium by examining the DPDW, a result that has not heretofore been achieved in the art.

It should be noted that when deriving Equation (1), the differential from of Fick's law and photon flux conservation principles were used. In a preferred embodiment of imaging by examining the scattering and diffraction refraction of DPDW, the effects of absorption of the DPDW can be ignored, and it can be assumed that the time it takes for light to travel a single random walk step is much shorter than the modulation period. In this case, the oscillatory part of the light energy density $U_\omega(r)$obeys the Helmholtz equation, i.e., $(\nabla^2+k^2)U_\omega(r)=0$. The only significant difference of DPDW propagation in comparison to conventional wave phenomena is that $k^2=i(\omega/D)$, and therefore k is complex.

The spatial part of $U_{ac}(r,t)$ in Equation (1) is simply the Green's function solution of the Helmholtz equation with the appropriate k. Therefore, some of the basic theorems that apply to solutions of the Helmholtz equation will apply to DPDW propagation in a turbid medium. For example, a Kirchoff integral can be constructed for these waves using the Green's function solution. This provides a formal method by which to calculate the wave amplitude and phase at various distances from a "diffracting" aperture as has been discussed in this Part II. To the extent that the Kirchoff integral embodies the basic Huygens-Fresnel principle, contributions of different elements of a scattering surface arising from damped, spherical point sources will be observed. This also implies that the focusing of DPDW will have the same limitations due to diffraction as in the case of light propagating in a standard optical medium. Thus, imaging of tumor-like inhomogeneities in tissue can be accomplished in accordance with the present invention by examining the refractive, diffractive and scattering properties of DPDW incident to the tissue.

III. Imaging by Examining Re-Radiated DPDW

The inventors of the subject matter herein claimed and disclosed have also discovered that examining re-radiated DPDW from a fluorescent inhomogeneity in a turbid medium provides methods of imaging inhomogeneities in the medium. Many types of tumors which occur in the human body comprise inhomogeneities which can be made to fluoresce after being irradiated with DPDW, and therefore, the inventors have determined that re-radiated DPDW provide an excellent means of locating tumors.

In order to observe re-radiated DPDW and image an object, the model biological material Intralipid is used. An amplitude modulated 200 MHz or 50 MHz laser diode ~3 mW, 780 nm is fiber-coupled into the medium, and another optical fiber is used to detect diffuse photons as a function of position within the medium. Using the standard heterodyne techniques discussed earlier, the phase and amplitude of the DPDW in the medium can be observed.

Figure 5:
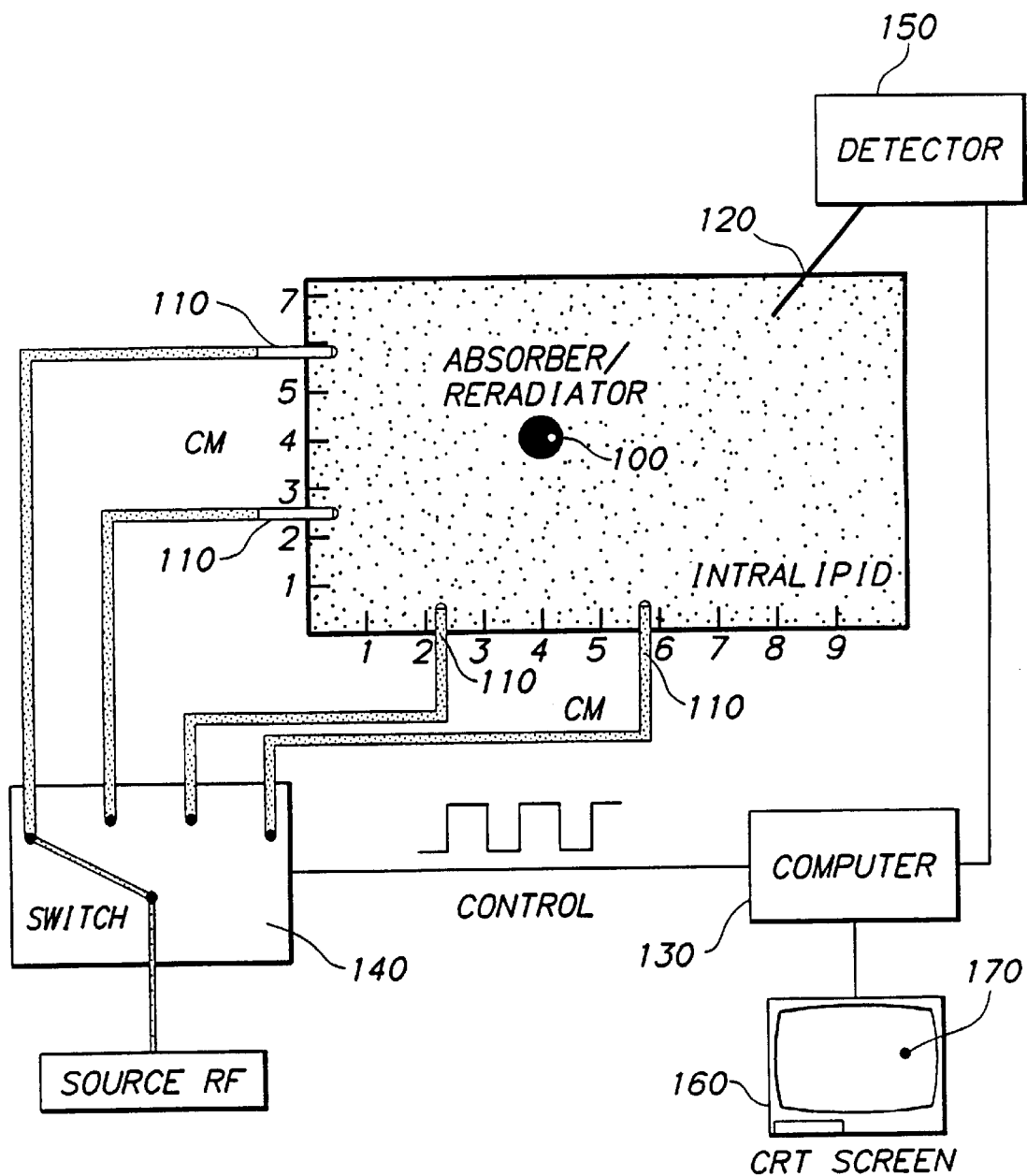
FIG. 5 is a schematic representation of a "time-sharing" system for imaging diffuse photon density waves re-radiated from a fluorescent object.

A preferred apparatus for imaging inhomogeneities in turbid media by detecting re-radiated DPDW is shown schematically in FIG. 5. The absorber/radiator shown at 100 preferably comprises a shell filled with Intralipid at a concentration of 0.4 mg/L Indocyanine green dye which is less than one tenth of the concentration commonly used in human subjects to test hepatic function. In this embodiment, multiple sources 110 and a single detector 120 are used to determine the center of the fluorescent object 100.

Computer processor 130 preferably outputs a control signal to switch 140 which controls the sequential activation of each of sources 110. A detector 150 which most preferably comprises a photomultiplier tube is interfaced both to detector fiber 120 and computer processor 130. In a further preferred embodiment, detector 150 is a Hamamatsu R928 or R1645u photomultiplier tube which also comprises a high voltage power supply that ensures adequate gain to computer processor 130 so the computer processor 130 can process the data received from detector fiber 120. A display device 160, preferably a CRT screen, is interfaced to computer processor 130 and outputs an image 170 of object 100.

To obtain image 170, a fluorescent object 100 is irradiated with multiple sources 110 of DPDW. It is then preferred to measure the amplitude (or phase) of the re-radiated light. The partial amplitude resulting solely from source i, is dependent on the $i^{th}$ source-object separation, the quantum efficiency of the dye in the object 100, and the object 100—detector 120 separation. Therefore:

$$|U_i| \propto \xi \frac{\exp(-k|\vec{r}_i - \vec{r}_o|)}{|\vec{r}_i - \vec{r}_o|} \frac{\exp(-k'|\vec{r}_o - \vec{r}_d|)}{|\vec{r}_o - \vec{r}_d|},$$

where $\xi$ is the quantum efficiency of the dye, $\vec{r}_i$ is the position of the $i^{th}$ source, $\vec{r}_o$ is the position of the object center, $\vec{r}_d$ is the detector position, and k (k') is the wave vector magnitude of the DPDW at 780 nm (830 nm).

The individual sources 110 are separately turned on and off, and the re-radiated amplitude for each object separation is measured. Since the source positions $\vec{r}_i$, and the detector position $\vec{r}_d$ are known, it is possible to estimate the object's position by finding the value of $\vec{r}_o$ that gives the best agreement with the measured ratio $|U_i|/|U_j|$. Generally, three sources 110 are necessary to localize the object in two dimensions. However, it is more preferable to use four or more sources to improve the signal-to-noise ratio of the imaging system. Using four sources 110 as shown in FIG. 5, it is possible to localize the center of the 1 cm spherical object 100 to within 0.4 cm. This two-dimensional localization is easily extended to three dimensions, as will be recognized by those with skill in the art.

Figure 6A:
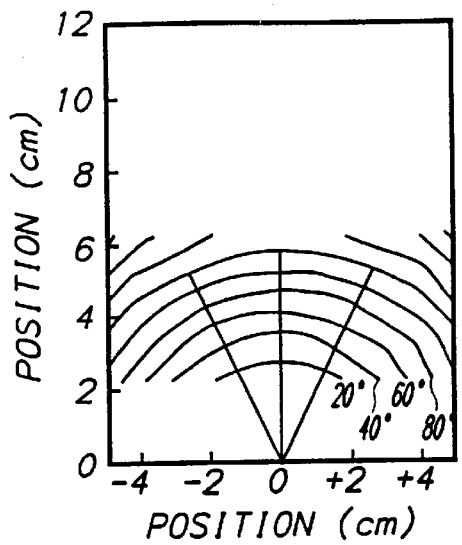
FIGS. 6A is a graph of phase contours of the disturbance produced by a fiber point source in a turbid medium.

Referring to FIG. 6A, constant phase contours of the disturbance produced by the fiber point source located at the origin of the system are illustrated. In a more preferred embodiment, re-radiated DPDW are obtained by filling a spherical glass shell with the absorbing dye Indocyanine green, and then illuminating the sphere with DPDW in the Intralipid solution. The dye is preferably chosen to absorb radiation at the source wavelength of 780 nm, and very soon thereafter re-radiate photons at a red-shifted energy, 830 nm. Because the dye has a lifetime of less than 1 nsec compared to the 5 nsec period of the source, the re-radiated energy is in the form of a DPDW at the red-shifted energy.

Figure 6B:
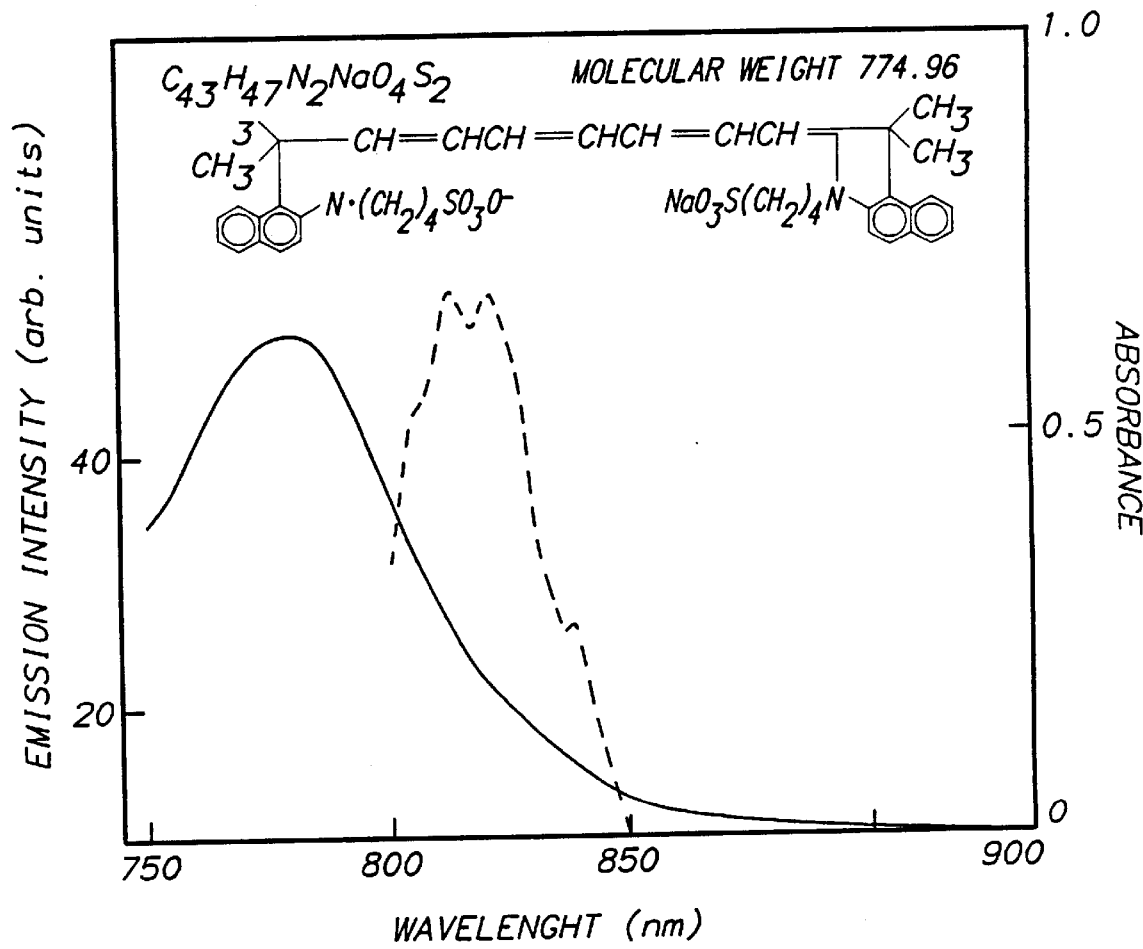
FIG. 6B is a graph of the absorption and emission characteristics of a fluorescent dye contained in a spherical shell within the turbid medium.
Figure 6C:
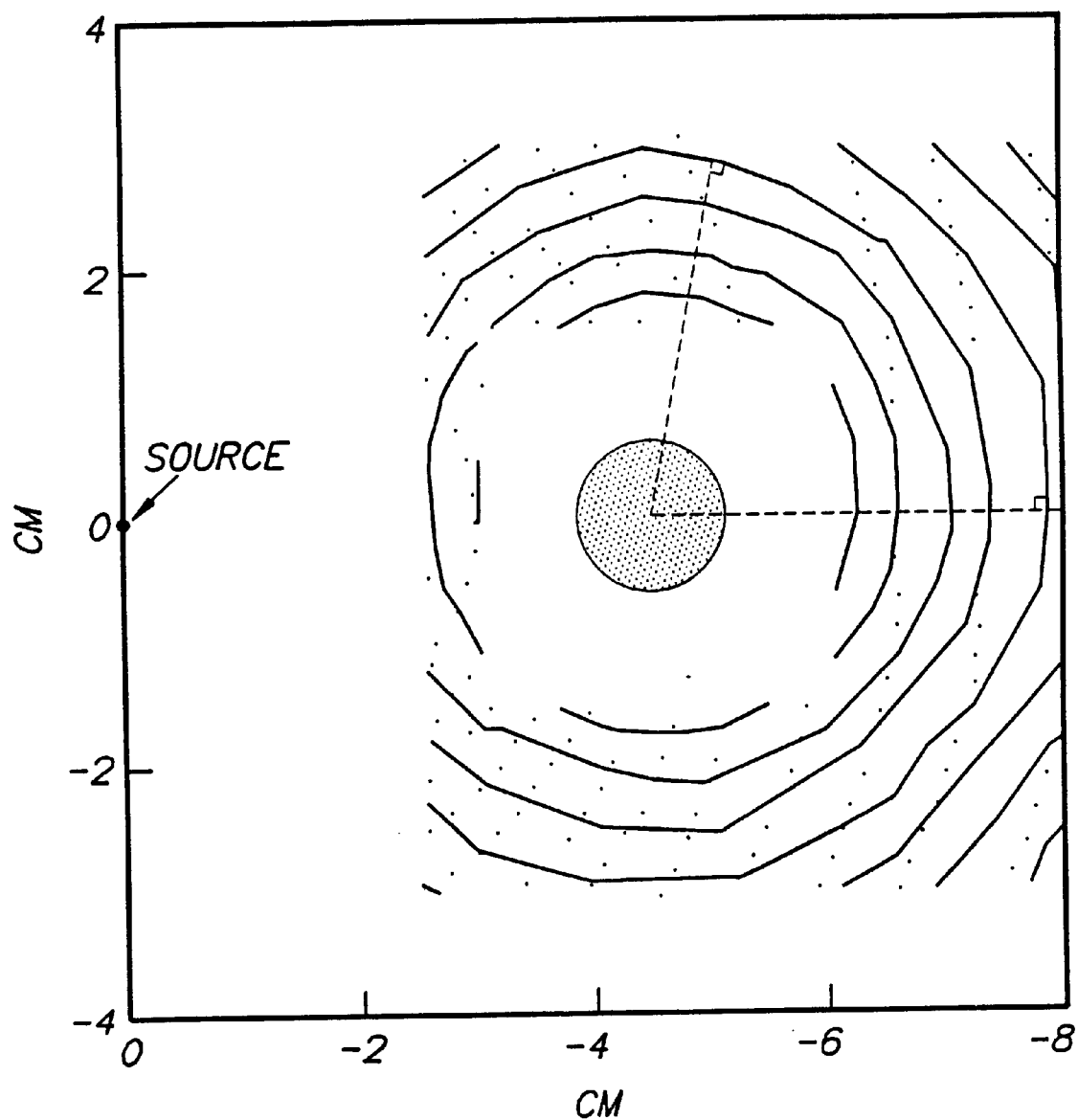
FIG. 6C is a graph of measured constant amplitude phase contours for diffuse photon density waves emitted from a source into a turbid medium, and re-radiated diffuse photon density waves.

The absorption and emission characteristics of the dye are shown in FIG. 6B wherein the inset is the chemical formula of the dye material. The Intralipid solution surrounding the obstacle has a concentration of 0.1% giving a source diffuse photon density wavelength of ~18 cm. A point source at the origin generates the incident DPDW. Constant amplitude contours of the incident wave in the presence of the obstacle are shown in FIG. 6C (dashed lines). In a more preferred embodiment, two spectral filters centered on 830 nm (Schott glass filters, RG830) are provided to enable the incident and re-radiated DPDW to be separated.

In FIG. 6C, the measured constant amplitude contours of the wave at 830 nm are shown as solid lines, and the measured incident amplitude contours at 780 nm are shown as dashed lines. The dashed lines demonstrate the DPDW character of the re-radiated waves. The re-radiated wave originates from within the absorbing object. As can be seen from the contours, the DPDW wavelength at 830 nm is somewhat longer than the DPDW wavelength at 780 nm. This is a function of the relatively larger diffusion coefficient for 830 nm light in Intralipid. Thus, a type of fluorescence of DPDW has occurred and the inhomogeneity is converted into a source of secondary DPDW.

Figure 7:
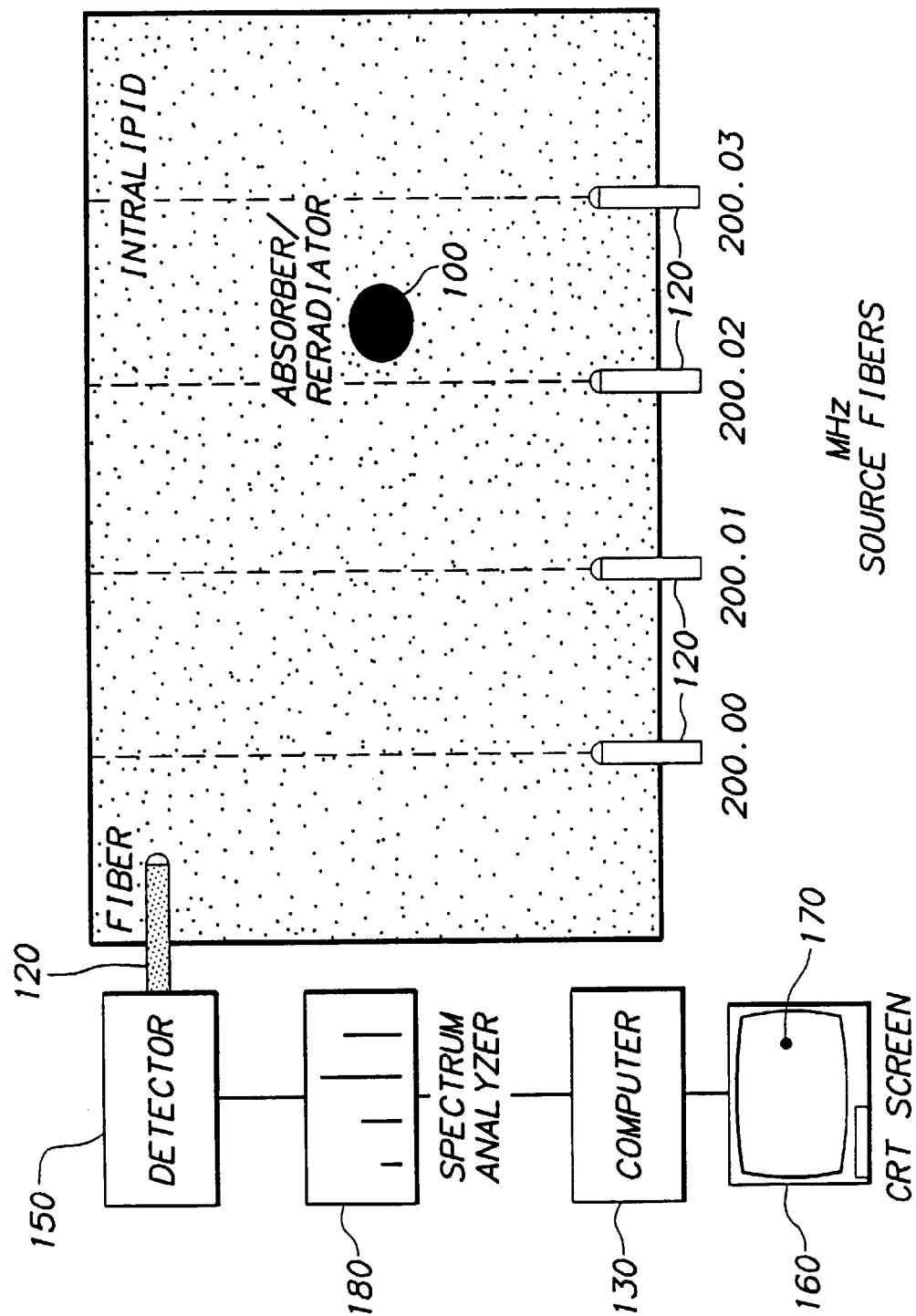
FIG. 7 is a schematic representation of a "frequency-encoded" system for imaging diffuse photon density waves re-radiated from a fluorescent object.

An alternative embodiment to the "time-sharing apparatus" for imaging using re-radiated DPDW described by FIG. 5 is a "frequency encoded apparatus" shown in FIG. 7. In this embodiment, each source 120 is modulated by a slightly different modulation frequency, $f_i$, (i.e., $f_i$=200.00+k (0.01)

MHz) and is kept on at all times. In this way, a modulation power spectrum is associated with each spatial location in the sample. By measuring the power spectrum of the re-radiated light as a function of modulation frequency with a spectrum analyzer 180, the position of object 100 can be determined using essentially the same analysis as described above with respect to the apparatus of FIG. 5. This type of imaging is similar to MRI in that a frequency spectrum emitted by an object is converted to the spatial location of the object.

Figure 8A:
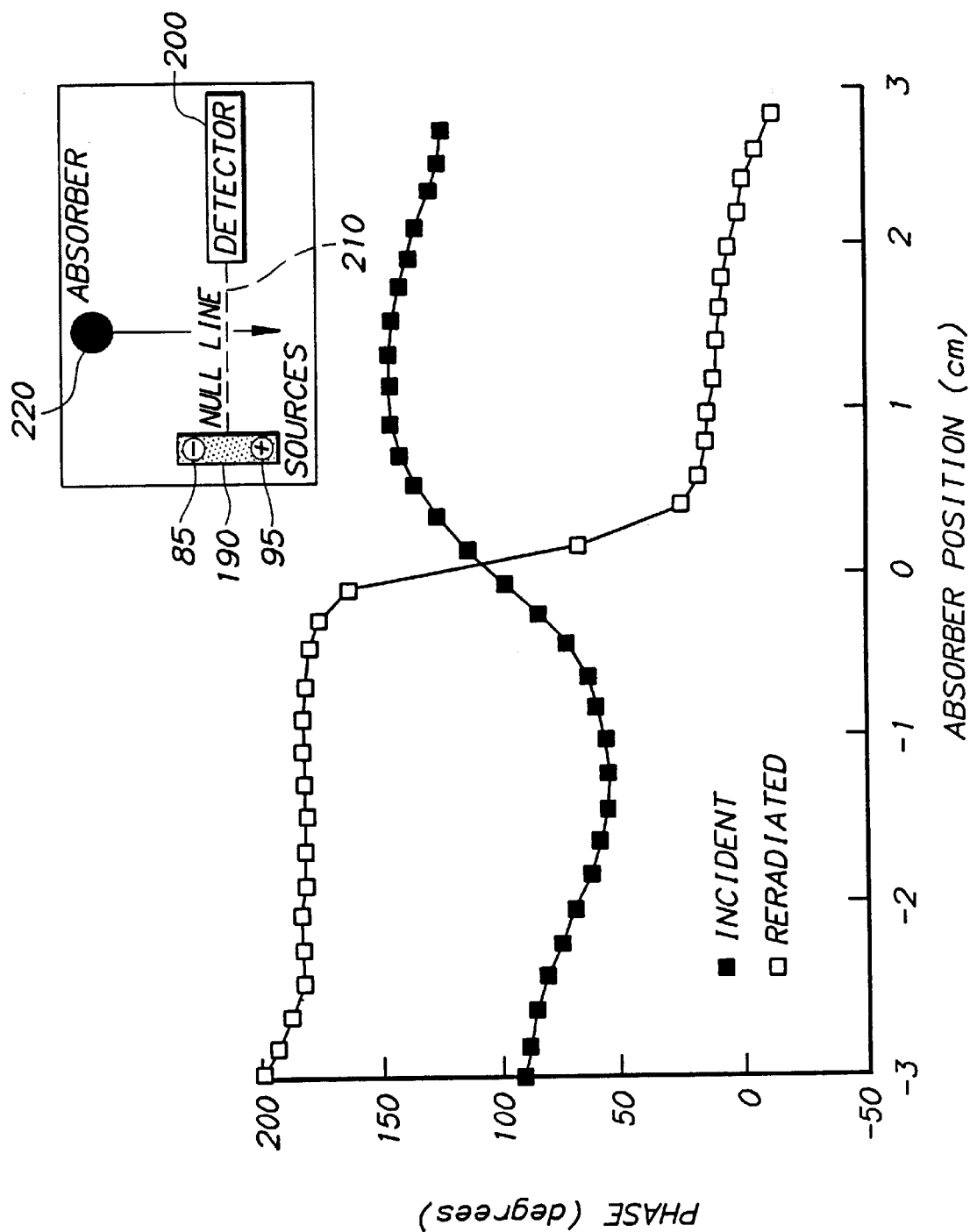
FIGS. 8A and 8B are schematic representations of "phased-array" scanning systems for imaging re-radiated diffuse photon density waves and graphs of the object's position in the turbid medium and a null line associated with the phased-array.
Figure 8B:
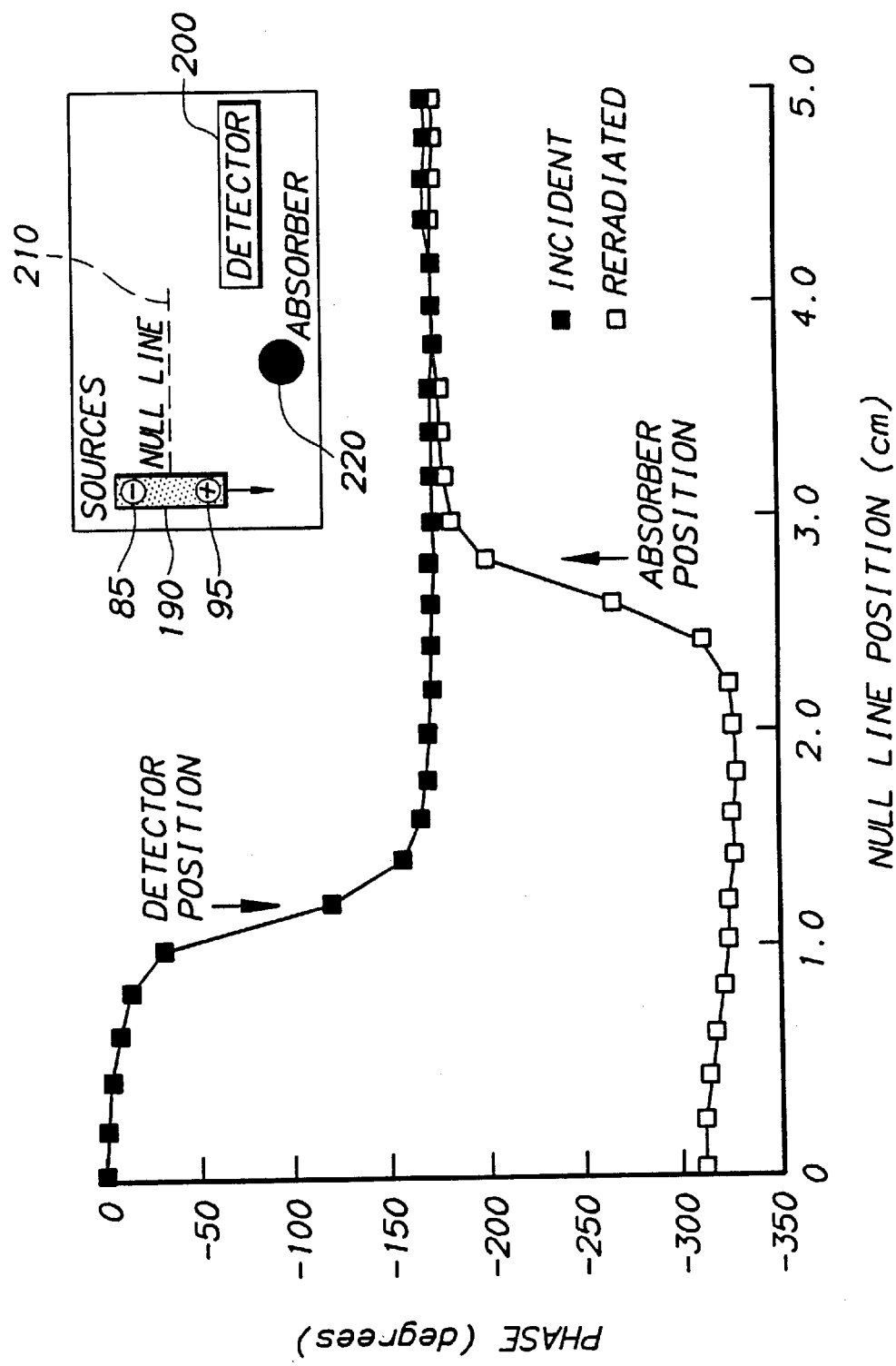

A third, alternative embodiment for imaging fluorescent objects that re-radiate DPDW is shown in FIGS. 8A and 8B. The apparatus of FIGS. 8A and 8B is qualitatively different than the time-sharing apparatus and frequency encoded apparatus of FIGS. 5 and 7 respectively, since it uses a scanning phased-array 190 and a single detector 200. Preferably, the phased-array 190 comprises two sources 85 and 95 that are substantially 180° out of phase with each other and that emit DPDW which interfere destructively to produce an amplitude null and a sharp 180° phase shift across a curve that describes this family of points called the "null line," shown schematically at 210.

By placing a detector 200 on the null line 210, and then moving an absorbing object 220 from one side of the null line 210 to the other, the object 220 will preferentially absorb light from the nearest source, and therefore distort the null line. When the absorber 220 is also a re-radiator, the complimentary effect is seen, that is, the object re-radiates more light derived from the closest source. In both measurements, the phase of the detected DPDW will undergo a 180° shift as the absorber crosses the original, undisturbed null line 210. These effects are demonstrated by the graphs of FIG. 8A. The re-radiated light displays a sharper phase transition, and a deeper amplitude null than that of the incident light, and the re-radiated wave exhibits a complimentary change as discussed above.

Interestingly, in the embodiment of FIG. 8A, the phase shift of the re-radiated light is always the same, independent of detector position. Thus, it is possible to hold the absorber 220 and the detector 200 stationary, and scan the null line 210 which will produce essentially the same results. Scanning the null line 210 can be achieved by mechanically translating the two sources 85 and 95 together.

Referring to FIG. 8B this effect is demonstrated for re-radiated light. A sharp phase shift at the location of the re-radiator 220 and null line 210 is detected. The phase transition of the incident light occurs near the position of detector 200. With knowledge of the position of the null line 210 as a function of time, a one-dimensional localization of the re-radiator can be achieved. By performing three scans down three perpendicular axes, three-dimensional localization of re-radiator 220 can be achieved. It is envisioned that the phased-array apparatus of FIGS. 8A and 8B will be simple to build and implement. Furthermore, imaging apparatus described herein will generally be much more economical to build than other imaging systems currently in use, such as MRI systems, PET systems, and CAT scanners.

IV. Imaging by Examining Lifetimes of Fluorophores in Turbid Media

Fluorescent lifetime-based quantitation of different biological parameters such as tissue oxygenation $pO_2$, pH value, and intracellular calcium concentration $[Ca^{2+}]$ have been proposed by several investigators. Localized fluorophore concentration or lifetime variation may signal an increased number of small blood vessels associated with rapid tumor growth, or the altered concentration of a fluorescence quencher that affects the fluorophore lifetime (e.g., the lowered concentration of oxygen from the high oxygen uptake in a rapidly growing tumor). Thus functional imaging of the variations of fluorophore concentration and lifetime may provide useful clinical information.

THEORY: THE FORWARD PROBLEM

A. Photon Diffusion in Infinite Homogeneous Media

First, we consider the forward problem of an infinite homogeneous turbid medium with a spatially uniform distribution of fluorophores. An intensity-modulated point light source with an optical wavelength that falls within the absorption band of the fluorophores creates an excitation diffuse photon density wave (DPDW) that excites the fluorophores. The fluorescent photons then add to create a fluorescent DPDW originating from the source fluorophore distribution. The fluorescent radiation is assumed to be well separated in energy from that incident photons so that we can safely ignore the possibility of the excitation of fluorophores by the fluorescent remission. We also assume that the excited fluorophores have a single lifetime.

1. Solution for a Point Source

In highly scattering media such as biological tissue, light propagation is well approximated by the photon diffusion equation that we adopt as a central assumption of our discussion, i.e., $$\nabla^2 \phi(r,t) - \frac{v\mu_a}{D}\phi(r,t) - \frac{1}{D}\frac{\partial \phi(r,t)}{\partial t} = -\frac{v}{D}S(r,t). \quad (1)$$

Here $\phi(r,t)$ is the photon fluence rate [photons/(cm$^2$s)], v is the speed of light in the turbid medium, $\mu_a$ is the absorption coefficient, $D=v/3\mu_s'$ is the photon diffusion coefficient where $\mu_s'$ is the reduced scattering coefficient, and $S(r,t)$ is the source term that is the number of photons emitted at position r and time t per unit volume per unit time.

For a point source at position $r_s$ with an intensity modulation frequency f, we have $S(r, t)=[M_{dc}+M_o \exp(-i\omega t)] \delta(r-r_s)$, where $M_{dc}$ and $M_o$ are the dc and ac parts of the source strength, respectively; $\omega$ is the angular modulation frequency, and $\omega=2\pi f$. The resultant DPDW can be written as the sum of dc and ac parts, i.e., $\phi(r, t)=\phi_{dc}(r)+\phi_o(r)\exp(-i\omega t)$. In $$\phi_0(r, r_s) = \frac{vM_0}{D}\frac{\exp(ik|r-r_s|)}{4\pi|r-r_s|}. \quad (2)$$

this paper we focus on the ac component. In an infinite homogeneous medium the ac solution to Eq.(1) is Here, the wave number k is complex, $k^2=(-v\mu_a+i\omega)/D$. We see that the solution of the excitation DPDW in an infinite homogenous system is a damped spherical wave.

Here, the fluorophore and chromophore absorptions are treated separately, but we assume that the change of scattering coefficient cause by the fluorophore is negligible for notational simplicity. (However, the fluorophore scattering effect is easily incorporated into the analytic solutions.) Absorption from tissue chromophores is characterized by absorption coefficient $\mu_a^c$. Absorption from exogenous fluorophores is characterized by an additional absorption coefficient $\sigma N_f$, where $N_f$ is the concentration of fluorophore and $\sigma$ is the fluorophore absorption cross section (which is essentially the same as the fluorophore extinction coefficient, see Section 3). Thus, in the presence of fluorophores the total absorption coefficient is the sum of these two coefficients, i.e., $\mu_a=\mu_a^c+\sigma N_f$.

2. Solutions for Fluorescent Diffusive Waves

Suppose that an intensity-modulated point source is at position $r_s$ in a homogeneous system. The fluorophores in the medium are excited by the incident DPDW, $\phi_o$, given in Eq. (2). Each excited fluorophore then acts as a secondary point source of fluorescent diffusive waves. Treating fluorophores as two-level quantum systems and ignoring saturation effects, we find that the steady-state number density of excited fluorophores at position r is $$N_e(r, r_s) = \frac{\sigma N_t \eta}{\Gamma - i\omega} \phi_0(r, r_s), \tag{3}$$

where $\sigma$ is the fluorophore absorption cross section at source wavelength $\lambda_{ex}$, $N_t$ is the fluorophore concentration, $\Gamma=1/\tau$ is the decay rate of an excited fluorophore, which is simply the reciprocal of fluorophore lifetime $\tau$, and $\phi_o$ is the incident photon fluence rate [Eq. (2)]; $\eta$ is the fluorescence quantum yield. For notational simplicity hereafter we assume excited fluorophores decay only through the radiation channel, i.e., $\eta=100\%$. These excited fluorophores decay with a rate $\Gamma$, and thus the source term for fluorescent DPDW at position r is $$S_f(r, r_s) = \Gamma N_e(r, r_s) = \frac{\sigma N_t}{1 - i\omega\tau} \phi_0(r, r_s). \tag{4}$$

Each fluorescence source generates a fluorescent DPDW that propagates to the detector at position r. The detected fluorescent DPDW is found by integrating over all fluorescence sources, i.e., $$\phi_{0f}(r, r_s) = \int S_f(r_1, r_s) \frac{v}{D_f} \frac{\exp(ik_f|r - r_1|)}{4\pi|r - r_1|} dr_1. \tag{5}$$

When the fluorophore distribution and lifetime are constant, one can solve the integral exactly by expanding the spherical waves in terms of spherical Bessel functions and spherical harmonics and then by using the appropriate orthogonality relations (see Appendix A). The analytic expression for the fluorescent DPDW in a homogeneous medium is $$\phi_{0f}(r, r_s) = \frac{v^2 M_0}{DD_f} \frac{\sigma N_t}{1 - i\omega\tau} \frac{1}{k^2 - k_f^2} \times \left[ \frac{\exp(ik|r - r_s|)}{4\pi|r - r_s|} - \frac{\exp(ik_f|r - r_s|)}{4\pi|r - r_s|} \right] \tag{6}$$

Note that the fluorescent DPDW is a superimposition of two spherical waves with different DPDW wave numbers: One has the DPDW wave number k at the source wavelength $\lambda_{ex}$, and the other has the DPDW wave number $k_f$ at the fluorescence wavelength $\lambda_{f1}$. The fluorescent DPDW is basically proportional to the fluorophore concentration (DPDW wave number k also depends on fluorophore concentration) and is explicitly related to the lifetime by a factor of $1/(1-i\omega\tau)$.

B. Photon Diffusion in Infinite Heterogeneous Media Containing a Spherical Heterogeneity A spherical object embedded in an otherwise homogeneous turbid medium may be of practical interest as a model for a tumor embedded in normal biological tissues. The analytic solution for fluorescent DPDW's in this case is useful in determining the fluorophore concentration contrast and lifetime changes necessary for detection of the object. Boas et al. have shown that the solution of DPDW's for a point source outside the sphere in a heterogeneous medium can be obtained by applying appropriate boundary conditions on the surface of the spherical object. We treat the analogous problem for the fluorescent DPDW.

The problem is more complicated, however, because the fluorescent point sources are now distributed in space. In general, the incident light source at $\lambda_{ex}$ is outside the sphere whereas the fluorescent sources emitting at $\lambda_{f1}$ can be inside and outside the sphere. We calculate the fluorescent DPDW generated by a point source inside and outside the sphere and then integrate the fluorescent DPDW over the corresponding source distribution to obtain the total fluorescent DPDW.

Before proceeding, we specify the following notation convention: All background quantities outside the sphere are denoted by subscript 1, e.g., $\phi_1$, $k_1$, $D_1$, and all quantities inside the sphere are denoted by subscript 2, e.g., $\phi_2, k_2, D_2$. Furthermore all fluorescence-related quantities are denoted by an extra subscript f, e.g., $\phi_{1f}$, $\phi_{2f}$, $k_{1f}$, $k_{2f}$, $D_{1f}$, $D_{2f}$. For simplicity we take the index of refraction $n_1=n_2$. This enables us to ignore the optical reflection and refraction effects on the surface of the sphere. The speed of light is then the same everywhere, $v_1=v_2=v$.

The main results are in Eq. (20) (the solution for the fluorescent DPDW generated by fluorophores inside a spherical object), Eq. (24) (the solution for the fluorescent DPDW generated by fluorophores outside the spherical object), and Eq. (25) [the sum of Eqs. (20) and (24), which is the solution for the fluorescent DPDW in an infinite heterogeneous turbid medium containing a spherical object]. Equations (26) and (27) are solutions for the fluorescent DPDW in a semi-infinite homogeneous system in which zero fluence rate boundary conditions and extrapolated zero fluence rate boundary conditions are used, respectively.

1. Solution for a Point Source

Figure 9B:
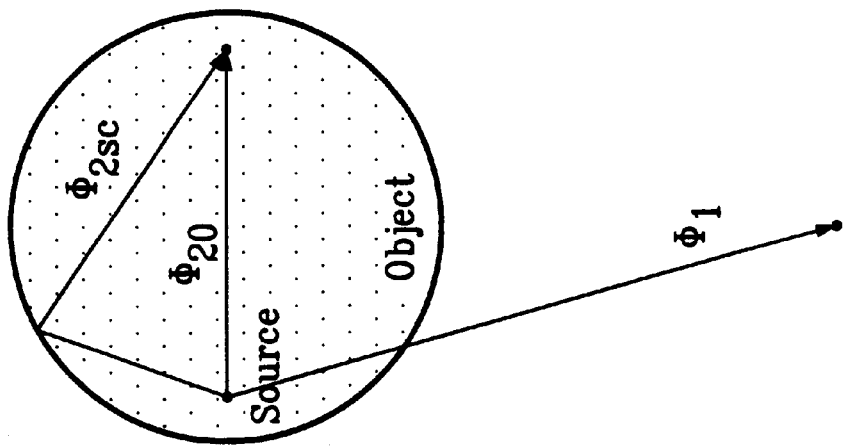
FIGS. 9A and 9B show source configurations in a heterogeneous medium containing a spherical object outside an inside the sphere, respectively.

Consider an infinite system with a spherical heterogeneity of radius a at the origin and a point source at $r_s$. In general, there are two possible source configurations: a point source outside the sphere ($r_s>a$) and inside the sphere ($r_s<a$) as shown in FIGS. 9A and 9B.

Figure 9A:
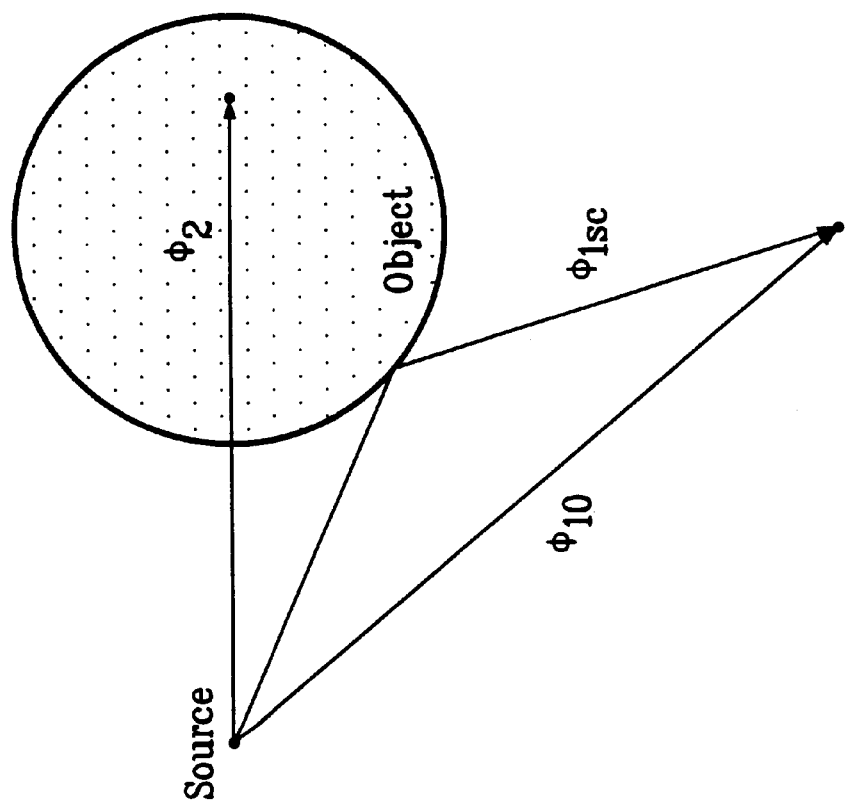

In FIG. 9A, the source is outside the sphere, and the solution of DPDW outside the sphere [Eq. (7)] is the sum of the homogeneous incident part, $\phi_{10}$, and the scattered part, $\phi_{1sc}$. The solution inside the sphere is $\phi_2$ as given by Eq. (8). In FIG. 9B, the source is inside the sphere, and the solution of DPDW outside the sphere is $\phi_2$ [Eq. (12)]. The solution inside the sphere is the sum of the homogeneous incident part, $\phi_{20}$, and the scattered part, $\phi_{2sc}$, as given by Eq. (13).

Physically we demand that the DPDW be finite at the origin (r=0) and vanish at infinity ($r\to\infty$).

For a point source outside the sphere the resultant DPDW solutions outside and inside the sphere are $$\phi_2(r, r_s) = \sum_{lm} B_{lm}(r_s) j_1(k_2 r) Y_{lm}(\Omega), \tag{7}$$

$$\phi_2(r, r_s) = \sum_{lm} B_{lm}(r_s) j_1(k_2 r) Y_{lm}(\Omega), \tag{8}$$

where $\phi_{10}$ is the incident wave with background parameters [Eq. (2)], i.e., $$\phi_{10}(r, r_s) = \frac{vM_0}{D_1} = \frac{\exp(ik_1|r-r_s|)}{4\pi|r-r_s|},$$

and $\phi_{1O}$ is the scattered wave. The functions $h_1^{(1)}(k_1r)$ and $j_1(k_2r)$ are spherical Hankel functions of the first kind and spherical Bessel functions, respectively. The $Y_{lm}(\Omega)$ terms are spherical harmonics, and $k_1$ and $k_2$ are DPDW wave numbers. We found the coefficients $A_{1m}$ and $B_{1m}$ by requiring that the diffusive photon fluence rate and normal flux be continuous at the surface of the sphere, i.e., $$\phi_1(a, r_s) = \phi_2(a, r_s), \tag{9}$$

$$D_1 \frac{\partial \phi_1(r, r_s)}{\partial r} = D_2 \frac{\partial \phi_2(r, r_s)}{\partial r}$$

$$|r = a \quad r = a$$

In this case we find that $$A_{lm}(r_s) = v \frac{-ik_1}{D_1} Q_1 h_1^{(1)}(k_1 r_s) Y_{lm} *(\Omega_s) M_0, \tag{10}$$

$$B_{lm}(r_s) = vR_1 h_1^{(1)}(k_1 r_s) Y_{lm} *(\Omega_s) M_0, \tag{11}$$

where $Q_1$ and $R_1$ are constants that depend on the optical properties at $\lambda_{ex}$, modulation frequency, and the radius of the embedded spherical object (a). Their definitions are in Appendix B.

For the case of a point source inside the sphere at $r_s(r_s<a)$, the solutions for the DPDW outside and inside the sphere are of the forms $$\phi_1(r, r_s) = \sum_{lm} C_{lm}(r_s) h_1^{(1)}(k_1 r) Y_{lm}(\Omega), \tag{12}$$

$$\phi_2(r, r_s) = \phi_{20}(r, r_s) + \phi_{2sc}(r, r_s) \tag{13}$$

$$= \phi_{20}(r, r_s) + \sum_{lm} D_{lm}(r_s) j_1(k_2 r) Y_{lm}(\Omega).$$

Using the same boundary conditions for the fluence rate and normal flux on the surface of the sphere [Eq.(9)], we obtain $$C_{lm}(r_s) = vR_1 j_1(k_2 r_s) Y_{lm} *(\Omega_s) M_0, \tag{14}$$

$$D_{lm}(r_s) = v \frac{-ik_2}{D_2} S_1 j_1(k_2 r_s) Y_{lm} *(\Omega_s) M_0, \tag{15}$$

Where $S_1$ is a constant that depends on the optical properties at $\lambda_{ex}$, modulation frequency, and the radius of the object. Its definition is given in Appendix B. $R_1$ is the same as in Eq. (11).

2. Solutions for Fluorescent Diffusive Waves

We assume that the fluorophore distribution is piecewise uniform, i.e., the outside and inside fluorophore concentration $N_1$ and $N_2$ may be different but they are constant. We also assume that the excitation point source (at $\lambda_{ex}$) is outside the sphere at $r_s(r_s>a)$. The source term for fluorophores outside and inside the sphere will be of the form $$S_{1f}(r_1, r_s) = \frac{\sigma N_1}{1 - i\omega\tau_2} \phi_1(r_1, r_s), \tag{16}$$

$$S_{2f}(r_2, r_s) = \frac{\sigma N_2}{1 - i\omega\tau_2} \phi_2(r_2, r_s), \tag{17}$$

respectively, where $\phi_1(r_1,r_s)$ is given by Eq. (7) and $\phi_2(r_2,r_s)$ is given by Eq. (8).

The fluorescent DPDW measured at position r outside the sphere and generated by a fluorophore inside the sphere at position $r_2$ with a source term $S_{2f}(r_2,r_s)$ is of the form of Eq.(12), i.e., $$\delta\phi_{1f} = (r, r_2, r_s) = \sum_{lm} \delta C_{lm}^f(r_2) h_1^{(1)}(k_{1f}r) Y_{lm}(\Omega), \tag{18}$$

where $$\delta C_{1m}{}^f(r_2) = vR_1{}^f j_1(k_{2f}r_2) Y_{1m}*(\Omega_2) S_{2f}(r_2,r_s) dr_2, \tag{19}$$

and $dr_2$ is the volume element around position $r_2$.

Figure 18A:
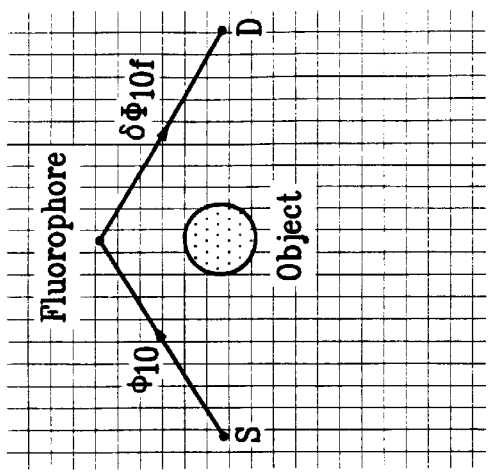
FIGS. 18A through 18E show diagrammatic representations of excited fluorophores in a heterogeneous system.
Figure 18B:
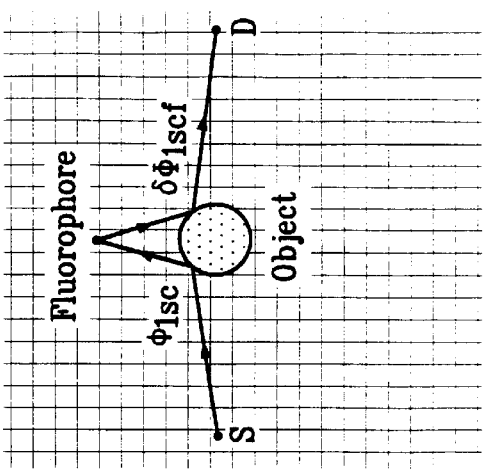
Figure 18C:
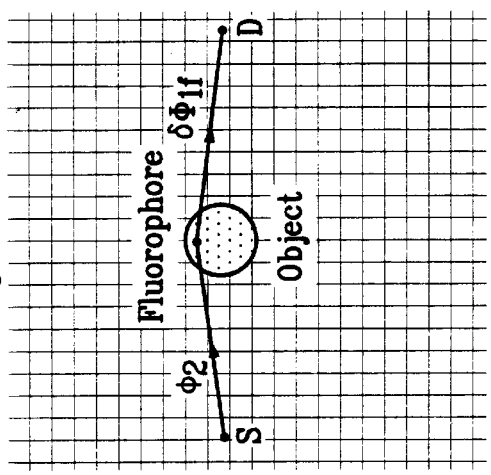
Figure 18D:
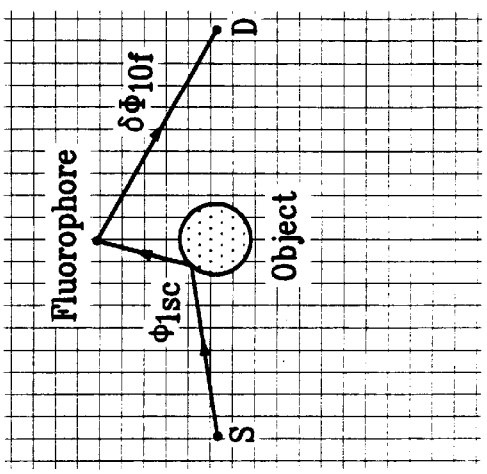
Figure 18E:
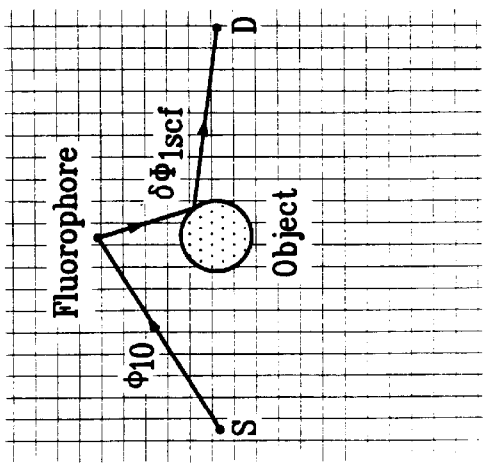

FIG. 18A shows that the fluorophore inside the sphere at $r_2$ is excited by incident DPDW $\phi_2(r_2,r_s)$ and the reemission propagates from $r_2$ to a point at r outside the sphere. Integrating Eq. (18) over the entire space inside the sphere (i.e., over all possible $r_2$), we derive the total contribution to the fluorescent DPDW from fluorophores inside the sphere, i.e., $$\phi_{1f} = \int_{Inside} \delta\phi_{1f}(r, r_2, r_s) \tag{20}$$

$$= M_0 v^2 \frac{\sigma N_2}{1-i\omega\tau_2} \frac{a^2}{k_2^2 - k_{2f}^2} \times \sum_{lm} \{[k_{2f} j_1(k_2 a) j_1'(k_{2f}'a) -$$

$$k_2 j_1'(k_2 a) \times j_1(k_{2f} a)] R_1 R_1^f h_1^{(1)}(k_{1f} r) h_1^{(1)}(k_1 r_s) \times$$

$$Y_{lm}(\Omega) Y_{lm} *(\Omega_s) \},$$

where constant $R_1^f$ has the same functional form as $R_1$ except that it depends on the optical properties at $\lambda_{f1}$ whereas $R_1$ depends on the optical properties at $\lambda_{ex}$. It is defined in Appendix B.

Next, we consider the fluorophores outside the sphere. The fluorescent DPDW measured at position r outside the sphere and generated by a fluorophore outside the sphere at $r_1$ with a source term $S_{1f}(r_1,r_s)$ is of the form of Eq. (7), i.e., $$\delta\phi_{1f}(r, r_1, r_s) = \delta\phi_{10f}(r, r_1, r_s) + \delta\phi_{1scf}(r, r_1, r_s) \tag{21}$$

$$= \delta\phi_{10f}(r, r_1, r_s) +$$

$$\sum_{lm} \delta A_{lm}^f(r_1) \times h_1^{(1)}(k_{1f}r) Y_{lm}(\Omega),$$

where $$\delta\phi_{10f}(r, r_1, r_s) = \delta\phi_{10f}(r, r_1) S_{1f}(r_1, r_s) dr_1 \tag{22}$$

$$= \frac{v}{D_{1f}} \frac{\exp(ik_{1f}|r-r_1|)}{4\pi|r-r_1|} \times S_{1f}(r_1, r_s) dr_1,$$

$$\delta A_{lm}^f(r_1) = \phi_{1scf}(r, r_1) S_{1f}(r_1, r_s) dr_1 \tag{23}$$

$$= \left[ v \frac{-ik_{1f}}{D_{1f}} Q_1^f h_1^{(1)}(k_{1f} r_1) Y_{lm} *(\Omega_1) \right] \times S_{1f}(r_1, r_s) dr_1,$$

and $dr_1$ is the volume element around position $r_1$.

The physical processes producing the fluorescent DPDW from fluorophores outside the sphere are shown in FIGS. 18A–18E. Integrating Eq. (21) over all space outside the sphere (i.e., over all possible $r_1$), we obtain the contribution to the fluorescent DPDW from fluorophores outside the sphere, i.e., $$\phi_{1f}(r, r_s) = \int_{outside} [\phi_{10f}(r, r_1) + \phi_{1scf}(r, r_1)] \frac{\sigma N_1}{1 - i\omega\tau_1} \times [\phi_{10}(r_1, r_s) + \phi_{1sc}(r_1, r_s)] d^3 r_1 \qquad (24)$$

$$= \frac{v^2 M_0}{D_1 D_{1f}} \frac{\sigma N_1}{1 - i\omega\tau_1} \frac{1}{k_1^2 - k_{1f}^2} \times$$

$$\left\{ \left[ \frac{\exp(ik_1|r - r_s|)}{4\pi|r - r_s|} - \frac{\exp(ik_{1f}|r - r_s|)}{4\pi|r - r_s|} \right] + \right.$$

$$\left[ (ik_{1f}) \sum_{lm} Q_1^f h_1^{(1)}(k_{1f}r) h_1^{(1)}(k_{1f}r_s) + \right.$$

$$(-ik_1) \sum_{lm} Q_1 h_1^{(1)}(k_1 r) h_1^{(1)}(k_1 r_s) +$$

$$(ik_1) \sum_{lm} Q_1 E_1 h_1^{(1)}(k_{1f}r) h_1^{(1)}(k_1 r_s) +$$

$$\left. (-ik_1) \sum_{lm} F_1 h_1^{(1)}(k_{1f}r) h_1^{(1)}(k_1 r_s) \right] \times$$

$$\left. Y_{lm}^*(\Omega_s) Y_{lm}(\Omega) \right\},$$

where the constant $Q_1^f$ has the same functional form as $Q_1$ except that it depends on the optical properties at $\lambda_{f1}$ whereas the constant $Q_1$ depends on the optical properties at $\lambda_{ex}$. Constants $E_1$ and $F_1$ depend on the optical properties at $\lambda_{ex}$ and the optical properties at $\lambda_{f1}$. The definitions of these constants are given in Appendix B.

Note that the spherical region is devoid of outside fluorophores. The contribution from the outside fluorophores may be constructed by subtracting the solution for a sphere (containing the outside fluorophore) from the homogeneous solution—the first two terms in the braces in Eq. (24) [see also Eq. (6)]. All other terms are due to the presence of the spherical object and correspond to various combinations of the other three paths in FIGS. 9D–9E. Equation (21) is exact, but unfortunately after the algebraic simplifications some of the terms in Eq. (24) arise from combinations of different paths, and the physical origins of these terms are not always easily visualized as in FIGS. 1(c)–1(f).

Finally the total fluorescent DPDW outside the sphere, $\phi_{hetero}^{f1}(r, r_s)$, generated by all of the fluorophores inside and outside the sphere, is given by the sum of Eqs. (20) and (24):

$$\phi_{hetero}^{f1}(r, r_s) = \phi_{1f}(r, r_s) + \phi_{1f}(r, r_s). \qquad (25)$$

Note that in Eq. (25), $\phi_{1f}(r, r_s)$ [see Eq. (20)] is the fluorescent DPDW generated by a fluorescing sphere with no background fluorophores whereas $\phi_{1f}(r, r_s)$ [see Eq. (24)] is the sum of the background term and the scattering terms. The total fluorescent DPDW is then the sum $\phi_{1f}(r, r_s)$ and $\phi_{1f}(r, r_s)$ [Eq. (25)].

In the forward calculation we take advantage of the symmetry of the system, e.g., if the light source is on the z axis, we have azimuthal asymmetry and we can remove the summation over m in Eqs. (20) and (24).

C. Semi-infinite Media and Numerical Verification of Analytic Solutions

In the above discussion we restricted our attention to infinite homogeneous and heterogeneous turbid media. The standard procedure for solving the diffusion equation for a semi-infinite homogeneous turbid medium is to approximate the exact zero partial current boundary condition with the extrapolated zero boundary condition. For the excitation DPDW, we satisfy the extrapolated zero boundary condition by using the method of images, i.e., the DPDW in the medium is calculated from the superposition of the DPDW's generated by the real and the image sources. This situation becomes more complicated for the fluorescent DPDW. The fluorescent DPDW is generated by a uniform distribution of fluorophores distribution of image fluorophores to calculate the fluorescent DPDW. Suppose fluorophores distribute in the upper space, z>0. The physical boundary of the fluorophores is the x-y plane at z=0. For extrapolated zero boundary conditions, where the photon fluence rate is approximated to be zero in the x-y plane at $z=(2/3\mu_s')$, the resultant image fluorophores then distribute in the lower space, $z<-(4/3\mu_s')$. In this case a gap appears between the physical boundary of the fluorophores at the z=0 plane and the corresponding image boundary of the image fluorophores at the $z-(4/3\mu_s')$ plane. There are no fluorophores or image fluorophores inside this gap. Therefore the integral equation of the form of Eq. (5) cannot be evaluated analytically. However, using a less accurate zero boundary condition (where the photon fluence rate is zero at the physical boundary), we can calculate the integral analytically (see Appendix C), i.e., $$\phi_{0f}^{si-z.b.c.}(r, r_s) = \phi_{0f}(r, r_s) - \phi_{0f}(r, r_s^{zbc}) \qquad (26)$$

where $r_s$ is the position of the real source and $r_s^{ebc}$ is the position of the image source with respect to the zero boundary; $\phi_{0f}(r, r_s)$ and $\phi_{0f}(r, *)$ are of the form of Eq. (6).

We have found that the extrapolated zero boundary condition can be implemented if we neglect the contribution of the gap. Neglecting the gap effect, we can take the solution in an infinite homogeneous system for a source at $r_s$ and the solution for an image source at $r_s^{ebc}$, then superpose these two solutions. The resultant fluorescent DPDW ($\phi_{0f}^{si-e.b.c.}$) for semi-infinite homogeneous systems with extrapolated zero boundary conditions has the same form as Eq. (26):

$$\phi_{0f}^{si-e.b.c.}(r, r_s) = \phi_{0f}(r, r_s) - \phi_{0f}(r, r_s^{ebc}), \qquad (27)$$

where $r_s$ is the position of the real source and the * is the position of the image source with respect to the extrapolated zero boundary; $\phi_{0f}(r, r_s)$ and $\phi_{0f}(r_s^{ebc})$ are the form of Eq. (6).

This is an extension of the result that we obtained in Appendix C using zero boundary conditions to approximate the exact zero partial current boundary conditions. Equation (27) turns out to be a very good approximation. Numerical calculations of fluorescent DPDW's at different modulation frequencies (f) where a finite difference algorithm is used have been performed to verify Eq. (27) for two fluorophore lifetimes (1 and 2 ns). The basic procedure is to solve the diffusion equation [Eq.(1)] for the fluorescence DPDW in the time domain by using the exact zero partial current boundary condition and then Fourier transform the data into the frequency domain. In the calculations the fluorophore concentration is assumed to be $N_f=0.1 \mu M$. The source and the detector are placed on the surface of the medium with a 2-cm separation, and the optical properties ($\mu_{a1}, \mu_{s1}', \mu_{a1f}, \mu_{a1f}', \sigma$) are given in Table 1. Results are shown in FIG. 3 in which we plot the theoretical amplitude and phase calculated by using Eq. (27) and the amplitude and phase calculated by using the finite difference method. The ratio of the normalized amplitude and the residual of the phase are also shown in FIG. 3. We find that the analytic solution of the fluorescent DPDW for a semi-infinite homogeneous system using an extrapolated zero boundary condition [Eq. (27)] agrees with the finite difference results with an accuracy of better than 3% in amplitude and 1.2° in phase up to an 800-MHz modulation frequency. Using a zero boundary condition [Eq. (26)] for the same system, we find that a little larger discrepancy, in particular, ~4% in amplitude and 1.5° in phase, was observed. These discrepancies are mainly due to a numerical computation error. If we reduce the grid size from $1/\mu_s'$ to $1/(2\mu_s')$ in the finite difference calculations, we find that these discrepancies decrease, e.g., less than 1.2% in amplitude and less than 1° in phase for a semi-infinite homogeneous system using an extrapolated zero boundary condition [Eq. (27)]. The tradeoff of using a smaller grid size is a much longer computation time. As we mentioned earlier, the analytic calculation is much faster than the numerical calculation. For $\tau=1$ ns in the above calculations, the analytic method takes ~0.1 s of CPU time (modulation frequency f varies from 0 to 1 GHz with a step of 50 MHz), but the finite difference method takes ~25 min. For a longer lifetime (e.g., $\tau=2$ ns) the numerical method requires a longer CPU time (e.g., ~1 h) whereas the analytic method still takes ~0.1 s of CPU time.

Figure 10A:
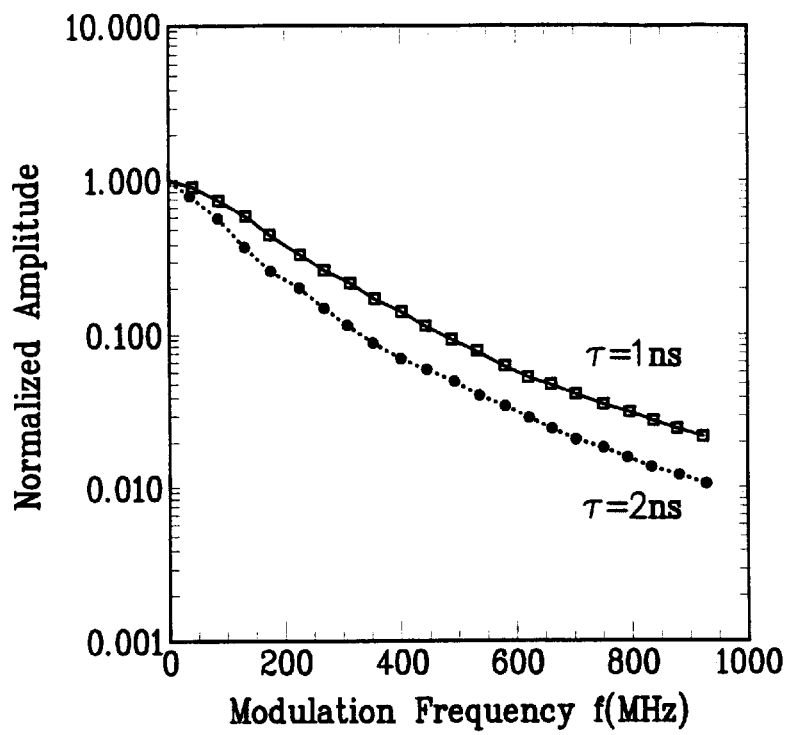
FIGS. 10A through 10D compare analytic solutions and finite difference methods for semi-infinite, homogeneous systems.
Figure 10B:
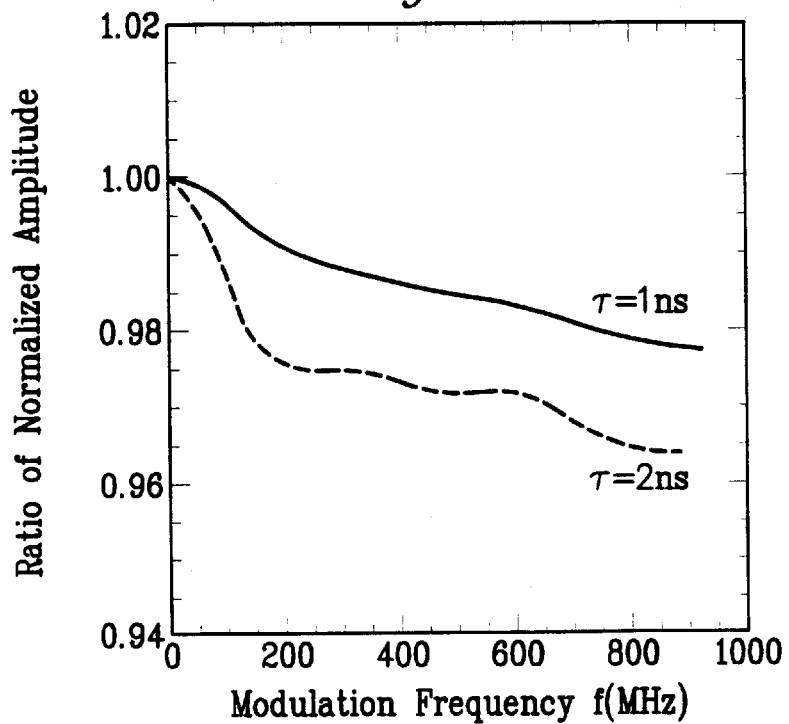
Figure 10C:
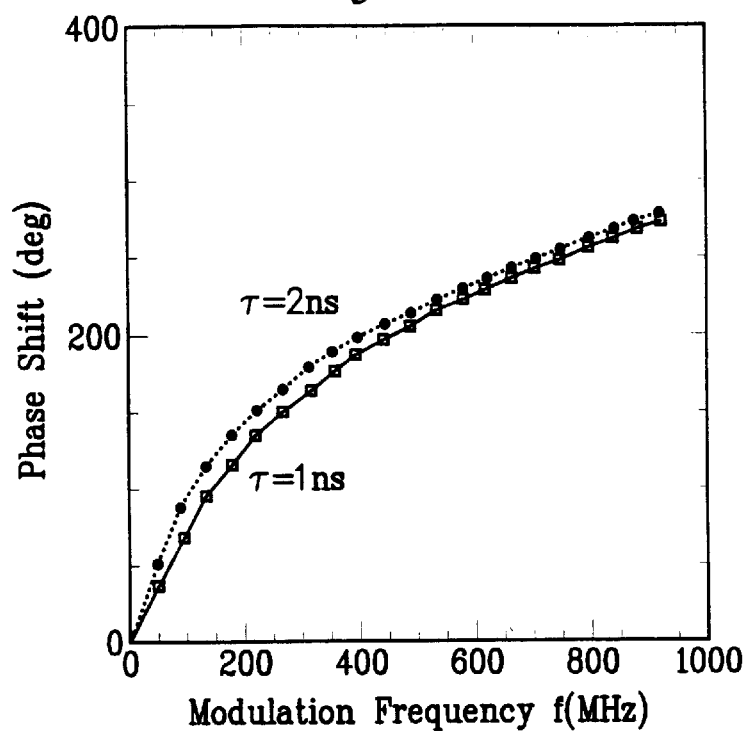
Figure 10D:
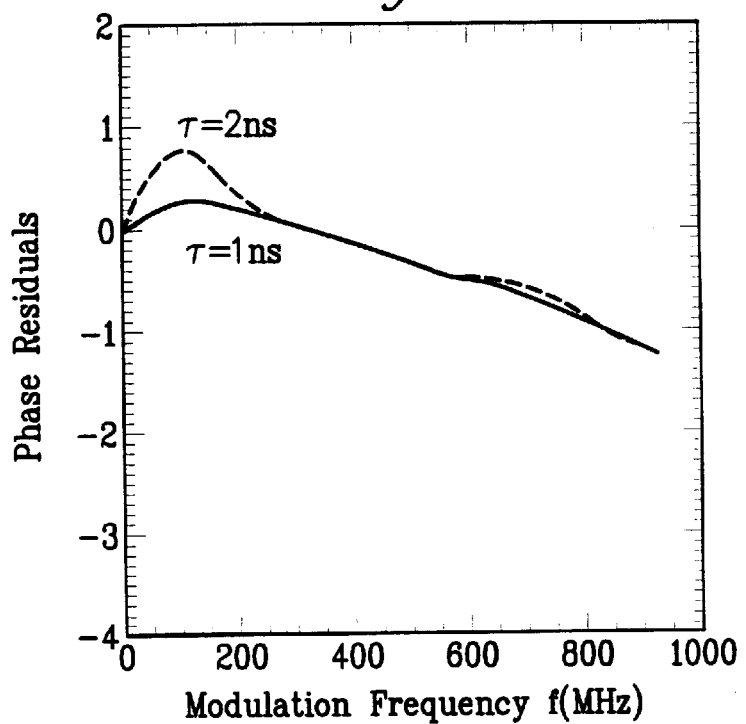

Referring to FIGS. 10A–10D, a comparison of the analytic solution [Eq. (27)] and the finite difference method for a semi-infinite homogeneous system is shown. The source and detector are place on the surface of the medium 2 cm apart. FIG. 10A is the amplitude normalized by the dc amplitude (f=0 MHz). The solid curve and the open circles represent normalized amplitudes for $\tau=1$ ns as calculated by the analytic solutions and the finite difference method, respectively. The dashed curve and filled circles represent normalized amplitudes for $\tau=2$ ns as calculated by the analytic solutions and the finite difference method, respectively. FIG. 10B shows the ratio of the normalized amplitude calculated by the finite difference methods and the normalized amplitude calculated by analytic solutions (solid curve, $\tau=1$ ns; dashed curve $\tau=2$ ns). FIG. 10C illustrates the phase with respect to the dc phase (which is zero). The solid curve and the open circles represent phases for $\tau-1$ ns calculated by analytic solutions and the finite difference method, respectively. The dashed curve and filled circles represent phases for $\tau=2$ ns calculated by analytic solutions and the finite difference method, respectively. In FIG. 10D, it can be seen that the phase residues that are the difference between the phase calculated by the finite difference method and the phase calculated by analytic solutions (solid curve, $\tau=1$ ns; dashed curve, $\tau=2$ ns).

As for the semi-infinite heterogeneous system, the situation will be much more complicated because we must consider not only the image source but also the image object as well as the image fluorophores. Nevertheless in analogy with semi-infinite homogeneous media observations, one can be encouraged to employ the same basic procedure as used in the above analysis. Finite difference calculations of the fluorescent DPDW in a semi-infinite heterogeneous turbid media containing a spherical object have been performed for different fluorophore concentration and lifetime contrasts. We found good agreement between the finite difference results and the results calculated by the analytic solutions, following the same basic procedure as for the semi-infinite homogeneous media. Consider a semi-infinite system with a 0.6-cm radius object 3 cm deep in the medium. The source and the detector are place on the surface of the medium and separated by 2 cm. An accuracy of better than 1.8% in amplitude and 1.2° in phase to an 800-MHz modulation frequency can be obtained when the optical properties given in Table 1 are used.

TABLE 1

Chromophore Optical Properties at $\lambda_{ex}$ and $\lambda_{fl}$ and Other Parameters°

| $\mu_{c1}{}^c$ | $\mu_{s1}'$ | $\mu_{o2}{}^c$ | $\mu_{s2}'$ | $\mu_{o1f}{}^c$ | $\mu_{s1f}'$ | $\mu_{o2n}{}^c$ | $\mu_{s2f}'$ | $\sigma$ (cm$^{-1}$M$^{-1}$) | $f$ (MHz) | $r_{sd}$ (cm) |
|---|---|---|---|---|---|---|---|---|---|---|
| 0.02 | 8.0 | 0.04 | 10.0 | 0.025 | 8.0 | 0.05 | 10.0 | $6 \times 10^4$ | 200 | 6 |

°The optical properties are in units of cm$^{-1}$; $r_{sd}$ is the source-detector separation.

3. Applications

Analytic solutions reveal the manner in which fluorescent DPDW's are related to the spatial distribution of fluorophore lifetimes and concentrations. We now apply these solutions to several problems of practical importance. First, we discuss the fitting procedure for determination of the fluorophore lifetime and concentration in homogeneous media. Next we calculate the fluorophore concentration contrast and the lifetime variation necessary to detect an object embedded in an otherwise homogeneous medium. Finally we compare the sensitivities of fluorophores as absorption contrast and fluorescent contrast for the detection of spherical objects in turbid media.

In general we take the fluorophore absorption cross section ($\sigma$) to be $\sim 10^{-16}$ cm$^2$ for near-IR excitation light. The absorption cross section is related to the extinction coefficient by Avogadro's constant, i.e., $\epsilon$(cm$^{-1}$M$^{-1}$)=$\sigma$(cm$^2$)$\times$ $N^{Avog} \times 10^{-3}$. In terms of the extinction coefficient the above absorption cross section is $6.0 \times 10^4$ cm$^{-1}$M$^{-1}$. Unless stated otherwise, we assume this value for the fluorophore absorption cross section. In the following simulations the fluorophore concentration in homogeneous media is assumed to be $N_f=0.1$ $\mu$M. The background concentration (outside the sphere) in the heterogeneous media is also assumed to be $N_1=0.1$ $\mu$M. Different concentrations inside the sphere are considered. We choose the concentration to be in the micromolar regime for three reasons: (1) Such concentrations are realistically expected for experiments in vivo. (2) Fluorescence saturation effects can be ignored. (3) The fluorophore absorption is comparable with the chromophore absorption when the fluorophore is used as an absorption contrast.

Figure 11A:
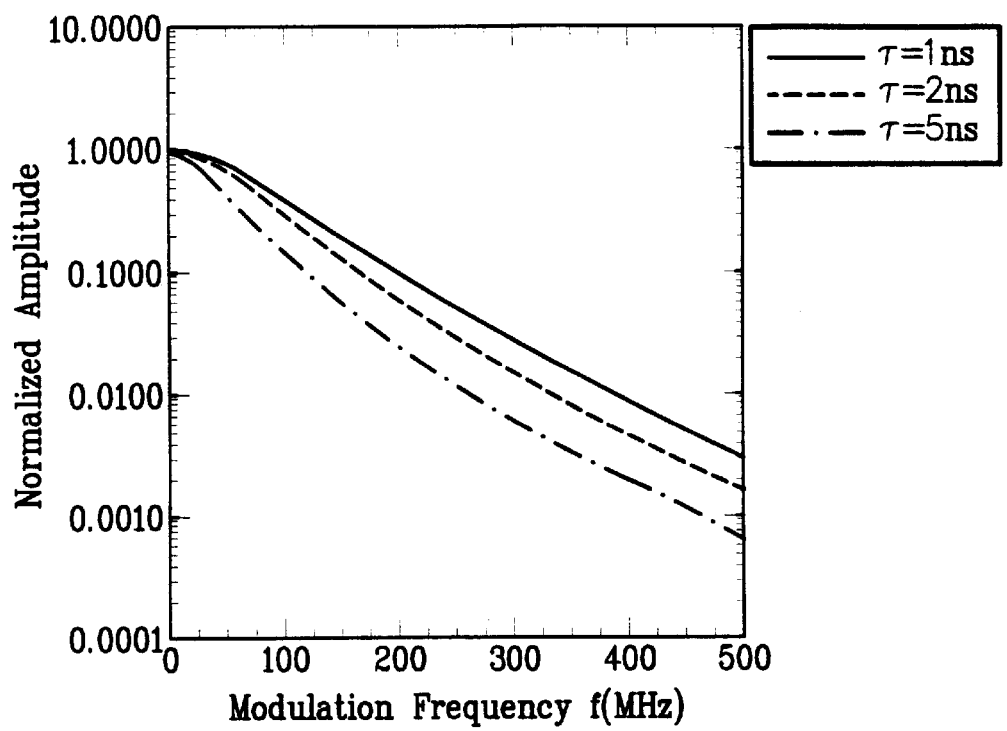
FIGS. 11A through 11B show fluorescent DPDW versus frequency in an infinite homogeneous turbid medium for different lifetimes.
Figure 11B:
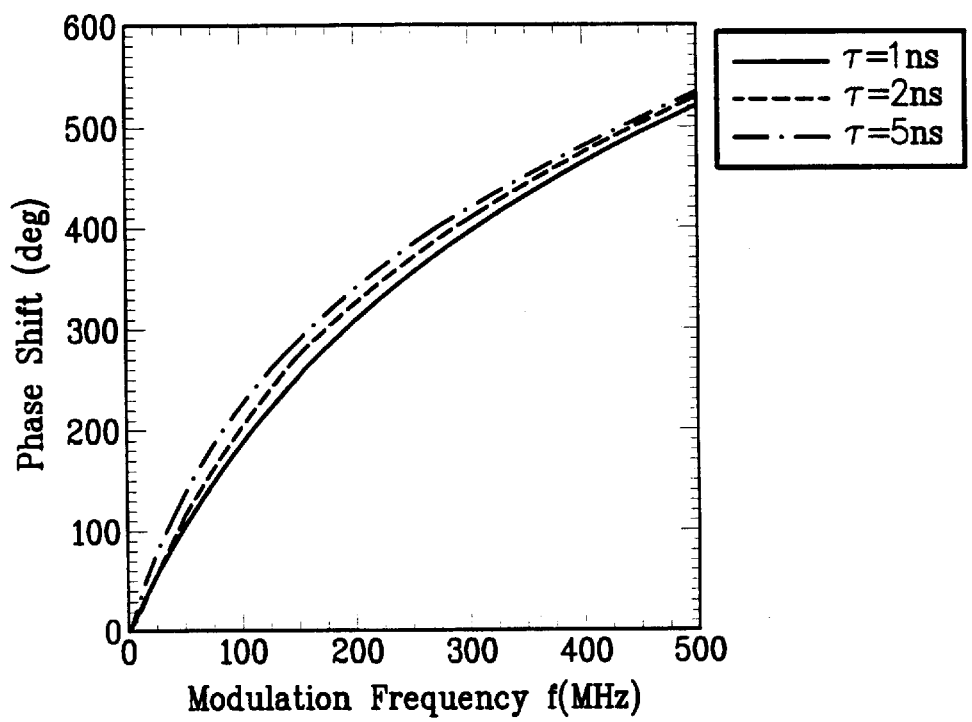

A. Fitting Procedure for Determination of Fluorophore Concentration and Lifetime in Homogeneous Systems Fluorophore lifetime is a good indicator of the fluorophore tissue environment (e.g., the pH or pO$_2$ value). One way to determine the fluorophore lifetime in homogeneous media is to measure the phase and/or the amplitude of the fluorescent DPDW at different modulation frequencies. The predicted dependence of the amplitude and phase of fluorescent DPDW on the modulation frequency (f) for three different lifetimes is illustrated in FIGS. 11A–11B. The differences in the curves indicate the sensitivity to fluorophore lifetime τ. The optical properties ($\mu_{a1}, \mu_{s1}', \mu_{a1f}, \mu_{s1f}', \sigma$), the source-detector separation ($r_{sd}$), and the modulation frequency (f) used in the simulation are given in Table 1. With experimental data, we can obtain accurate lifetimes and concentration by fitting the amplitude and phase curves of the fluorescent DPDW with the analytic solution [Eq. (6)] at multiple modulation frequencies. In such cases the tissue optical properties at $\lambda_{ex}$ and $\lambda_{f1}$ should be measured before adding fluorophores into the system to reduce the number of free parameters in the fit.

Referring FIGS. 11A–11B, fluorescent DPDW [Eq. (6)] versus the modulation frequency (f) in an infinite homogeneous turbid medium for three different lifetimes (τ=1,2 and 5 ns): FIG. 11A shows the normalized amplitude, and FIG. 11B phase shift. The amplitude is normalized by the amplitude at zero modulation frequency (f=0) for each curve at the corresponding fluorophore lifetime, and the phase is phase shifted with respect to the phase at the zero modulation frequency. Solid curves, τ=1 ns; dashed curves, τ=2 ns; dash-dotted curve, τ=5 ns. Source-detector separation rsd, 6 cm. The optical properties ($\mu_{a1}^c, \mu_{s1}'$ for incident DPDW at $\lambda_{ex}$ and $\mu_{a1f}'$ for fluorescent DPDW at $\lambda_{f1}$) are given in Table 1.

Using the same optical parameters and source-detector separation (6 cm) as in FIGS. 11A–11B, we calculate the amplitude and phase of the fluorescent DPDW for $N_t$=0.1 $\mu$M and τ=1.0 ns at multiple modulation frequencies (0–500 MHz in 50-MHz steps). We then add 2% random noise to the amplitude and 1° random noise to the phase. The noisy data are fitted with the analytic solution [Eq. (6)] where we assume that all the parameters are known except the fluorophore concentration and lifetime. For six independent least-square fittings, we obtain the fluorophore concentration, $N_t^{fit}$=(0.1002±0.0007) $\mu$M and lifetime $\tau^{fit}$=(1.003±0.007) ns. For the data with 5% amplitude noise and 5° phase noise, the fitted results are still very close to real values, e.g. $N_t^{fit}$=(0.1003±0.0017)$\mu$M and $\tau^{fit}$=(1.005±0.016)ns.

Another method suggested by others for lifetime measurements in homogenous turbid media is to introduce a reference fluorophore with a known lifetime. They pointed out that the unknown fluorophore lifetime can then be obtained from the relative phase shift between the fluorescent DPDW generated from fluorophores with unknown lifetime and the fluorescent DPDW generated from reference fluorophores with a known lifetime. This relationship is easily verified for homogeneous media where the analytic solution is used. In Eq. (6) we see that the phase of the fluorescent DPDW caused by the fluorophore lifetime is $\tan^{-1}(\omega\tau)$. If we assume that the optical properties are the same for the fluorophore with lifetime $\tau_2$ (unknown) and the fluorophore with lifetime $\tau_1$ (known), we obtain the relative phase shift $\theta_{21}$:

$$\theta_{21} = \tan^{-1}\left[\frac{\omega(\tau_2 - \tau_1)}{1 + \omega^2\tau_1\tau_2}\right] = \tan^{-1}(\omega\tau_2) - \tan^{-1}(\omega\tau_1), \quad (28)$$

which is in agreement with the result in Ref. 16. For a homogeneous system, Eq. (28) provides a simple relationship between the phases of the fluorescent DPDW's generated by two kinds of fluorophore with different lifetimes, and it is valid as long as the optical properties of the medium are the same for the two fluorophores.

Figure 12A:
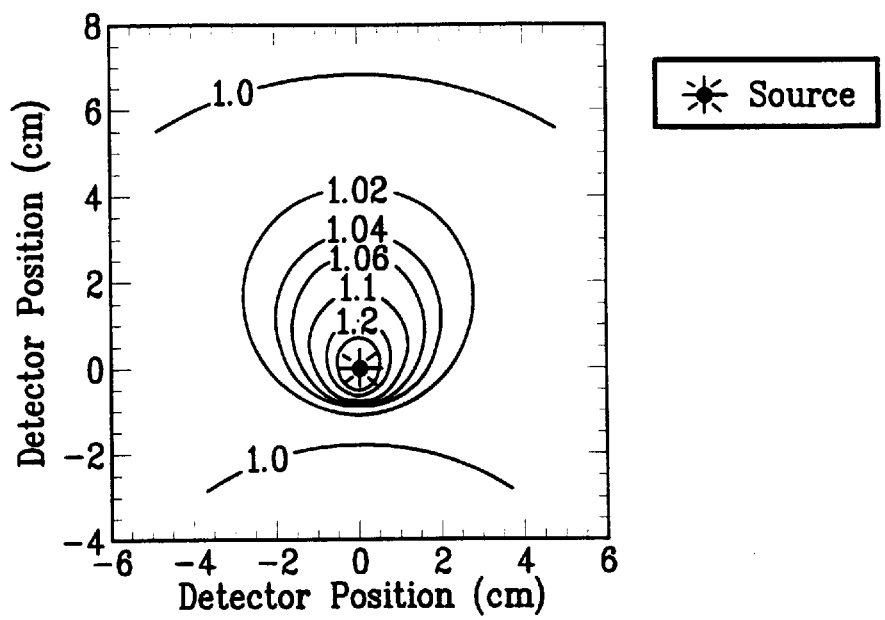
FIG. 12A plots contours of normalized amplitude, while FIG. 12B plots contours of phase shift.
Figure 12B:
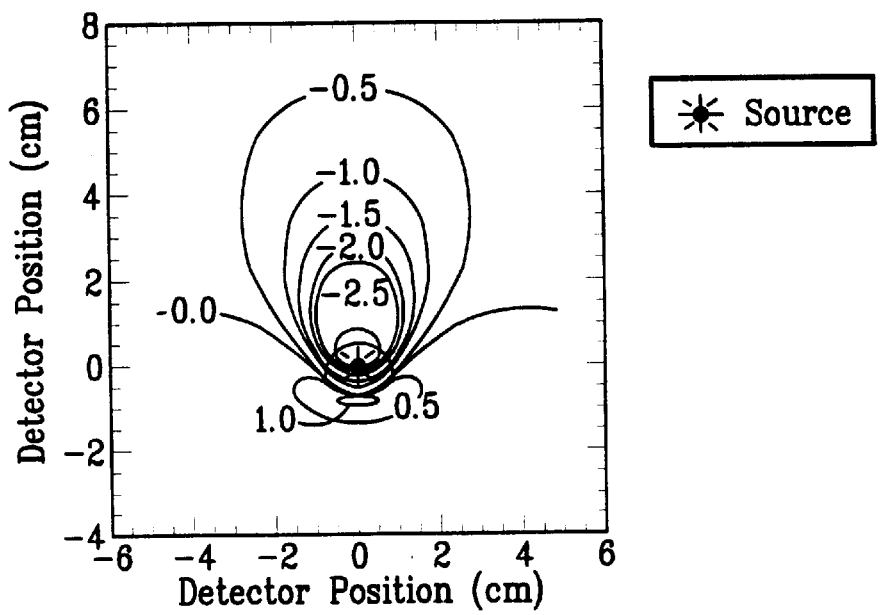

B. Required Contrast of Fluorophore Concentration and Lifetime for Detection and Characterization of a Spherical Heterogeneity The variations in fluorophore distribution and lifetime in normal and malignant tissues may give enhanced sensitivity and specificity for tumor detection. Using Eq. (25), we calculate the amplitude and the phase of the fluorescent DPDW for a heterogeneous system containing a spherical object. The required phase precision to detect such an object with fluorescent DPDW's is determined from the position-dependent phase difference between the fluorescent DPDW in the homogeneous medium and the fluorescent DPDW in the homogeneous medium with the same background optical properties. The required amplitude precision is found from a similar position-dependent normalized amplitude $\phi_{hetero}^{f1}/\phi_{0}$ [see Eqs. (6) and (25)]. FIGS. 12A and 12B show contour plots of the spatially dependent normalized amplitude and the phase shift for an object of 0.6-cm radius at the origin in a medium with the optical properties given in Table 1. FIG. 12A shows contours of normalized amplitude and FIG. 12B shows contours of phase shift. The source is located 3 cm from the object. A detector would scan in the plane that contains the source and the center of the object. In the calculation the lifetimes of the fluorophore outside and inside the sphere are assumed to be equal, i.e., $\tau_1=\tau_2=1$ ns, and the concentration contrast $N_2/N_1$ is assumed to be 5. We see that differential amplitude and phase signals from an object of 0.6-cm radius (within ~4 cm of the object) is detectable with the 0.1° phase and 0.1% amplitude measurement precision achievable with current technologies.

Figure 13A:
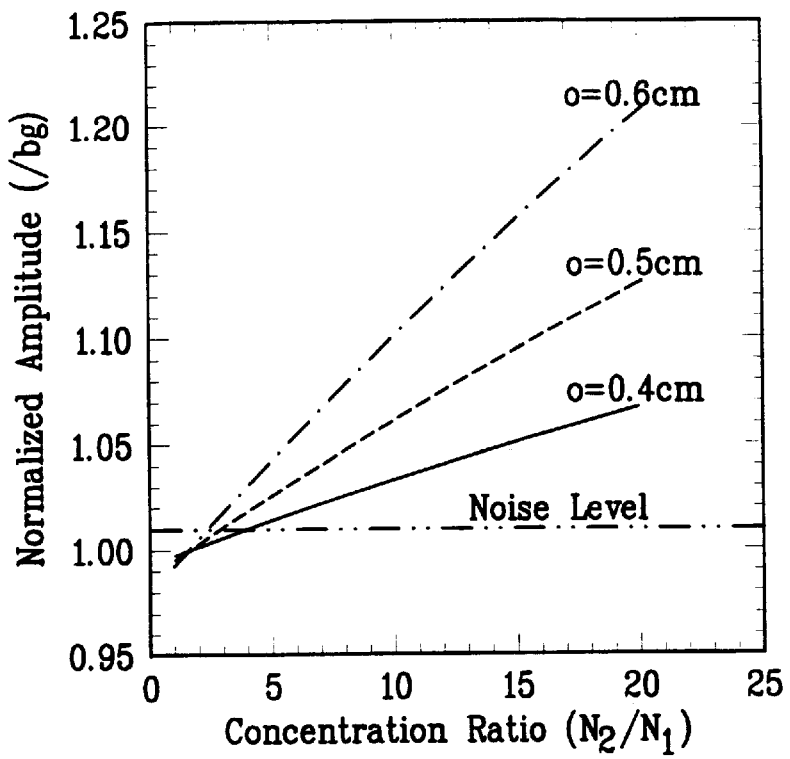
FIGS. 13A and 13B plot fluorescent DPDW versus fluorophore concentration contrast in a heterogeneous system.
Figure 13B:
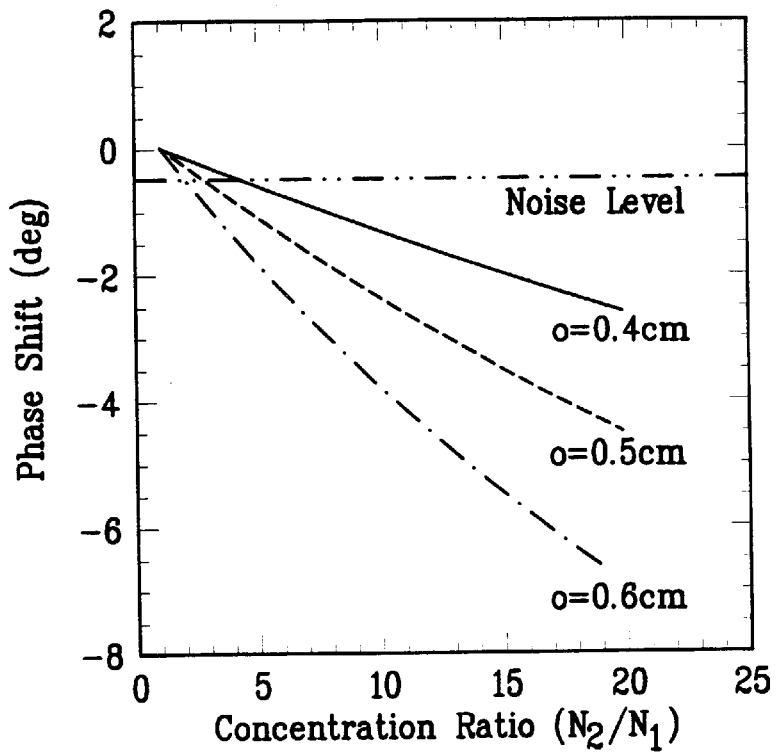

Some fluorophores may be tumor specific and the fluorophore concentration inside the tumor may be higher than in the surrounding normal tissues. Normalized amplitudes and phase shifts of the fluorescent DPDW versus fluorophore contrast $N_2/N_1$ are calculated for objects of three different sizes by using the parameters given in Table 1. The objects are always centered between the source and the detector. Results are shown in FIGS. 13A and 13B. FIG. 13A shows normalized amplitude; FIG. 13B shows phase shift. We find that, if our system is limited by 0.1% amplitude noise and 0.1° phase noise, a contrast, $N_2/N_1$~5, give us differentiable fluorescence signals for an object of 0.5-cm radius.

Figure 14A:
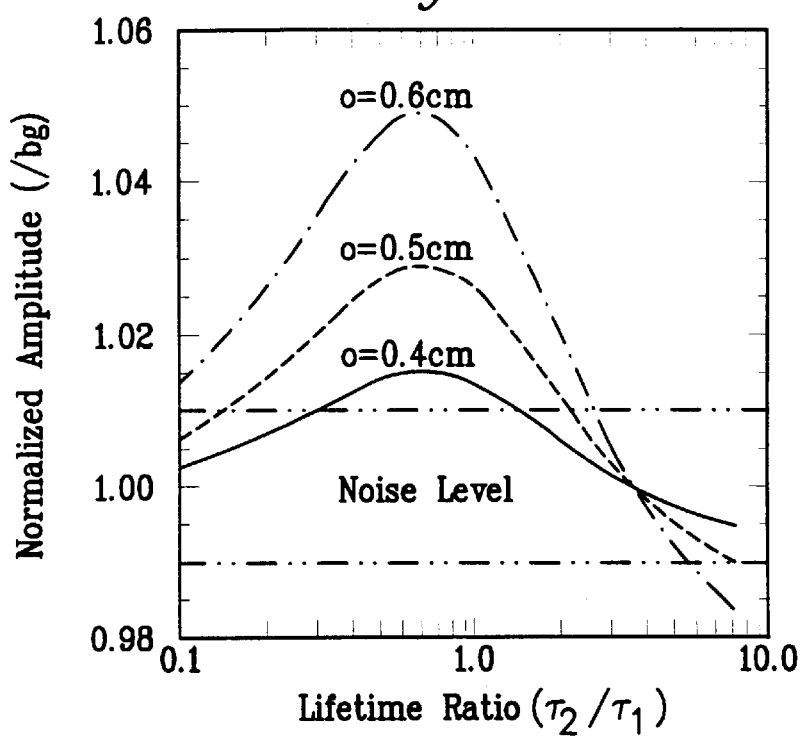
FIGS. 14A and 14B plot fluorescent DPDW versus a fluorophore lifetime change in a heterogeneous system.
Figure 14B:
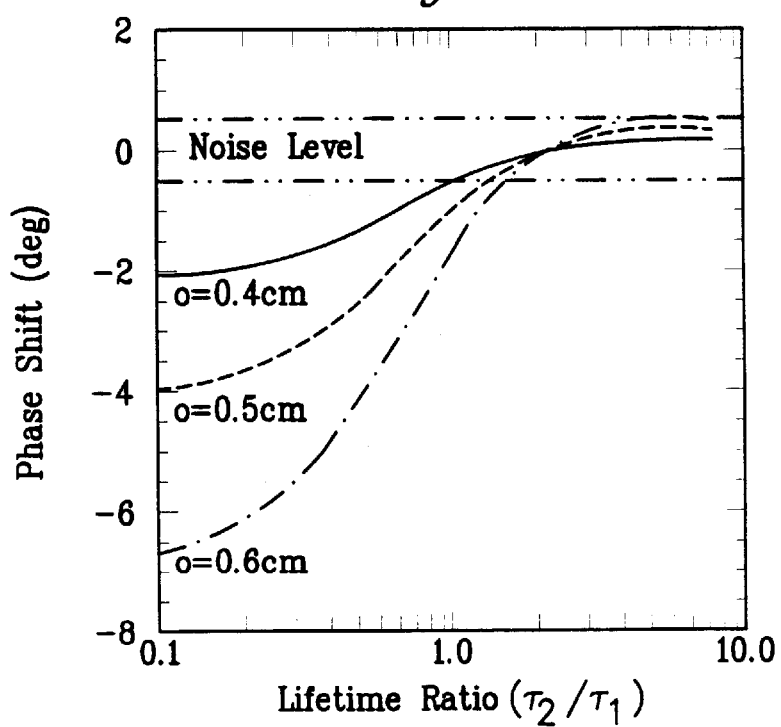

The fluorophore lifetime can be altered by the environment. This is another possible indicator for tumor detection. If the fluorophore lifetime inside the object ($\tau_2$) increases, the fluorescent DPDW amplitude decreases and the phase shift resulting from $\tau_2$ saturates for $\omega\tau_2>1$. If, on the other hand, $\tau_2$ decreases and $\omega\tau_2<1$, the amplitude and the phase are no longer sensitive to $\tau_2$. We see, however, that a regime exists wherein the change of $\tau_2$ gives enhanced sensitivity to the detection of the heterogeneity. In FIGS. 14A and 14B, the lifetime ratio ($\tau_2/\tau_1$) dependence of fluorescent DPDW's for three different size objects is shown, again centered between the source and the detector, using the parameters given in Table 1. We assume the fluorophore concentration contrast, $N_2/N_1$=5, in the calculation and find that when $0.2 \leq \tau_2/\tau_1 \leq 1.8$ the amplitude and phase provide signals above the defined noise level for the detection of an object of 0.5-cm radius.

If we assume that all the parameters are known except the fluorophore concentration and lifetime inside the object, e.g., $N_2$ and $\tau_2$, we can use the data as multiple modulation frequencies (0–500 MHz in 50-MHz steps, added with 2% amplitude noise and 1° phase noise) to fit for the concentration and the lifetime. In this case we find that $N_2$ and $\tau_2$, obtained from the fitting procedure are close to their real values, i.e., $N_2^{fit}=(0.508\pm0.015)$ $\mu$M and $\tau_2^{fit}=(1.530\pm0.060)$ ns where the real concentration and lifetime are $N_2=0.5$ $\mu$M and $\tau_f^{fit}=1.5$ ns. The errors in $N_2^{fit}$ and $\tau_f^{fit}$ are the standard errors for six independent fittings. In the calculation a spherical object of 0.6-cm radius is centered between the source and the detector, and the source-detector separation is 6 cm. Background fluorophore concentration and lifetime are assumed to be $N_1=0.1$ $\mu$M and $\tau_1=1.0$ ns, respectively. The optical properties are given in Table 1. Note that in practice the fitting procedure to obtain the fluorophore concentration and lifetime inside the object is more difficult, because there are more unknown parameters such as the optical properties inside the object and the size and the position of the object. Thus the fitting procedure above for heterogeneous media provides best-case estimates.

Figure 15A:
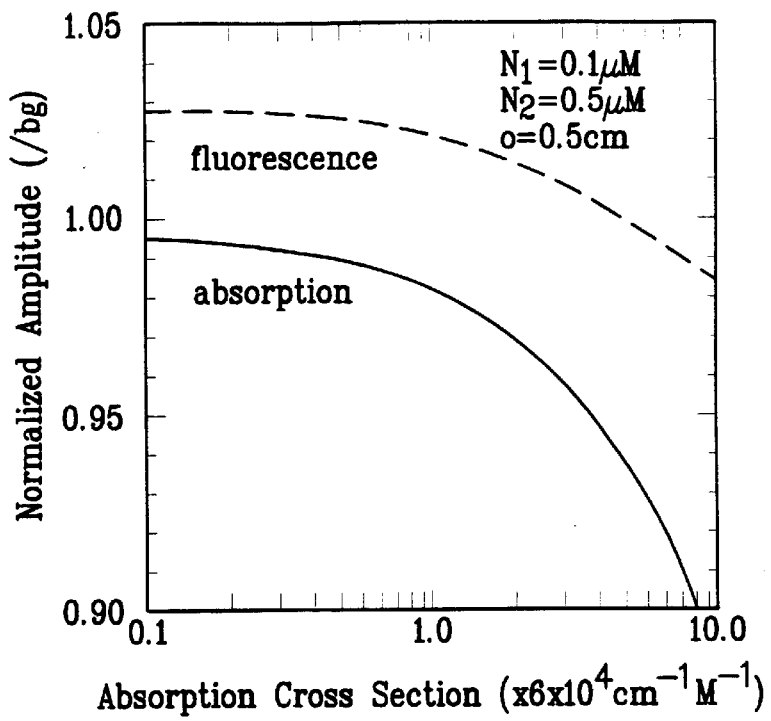
FIGS. 15A and 15B plot comparison absorption and fluorescence of fluorophores in a heterogeneous medium.
Figure 15B:
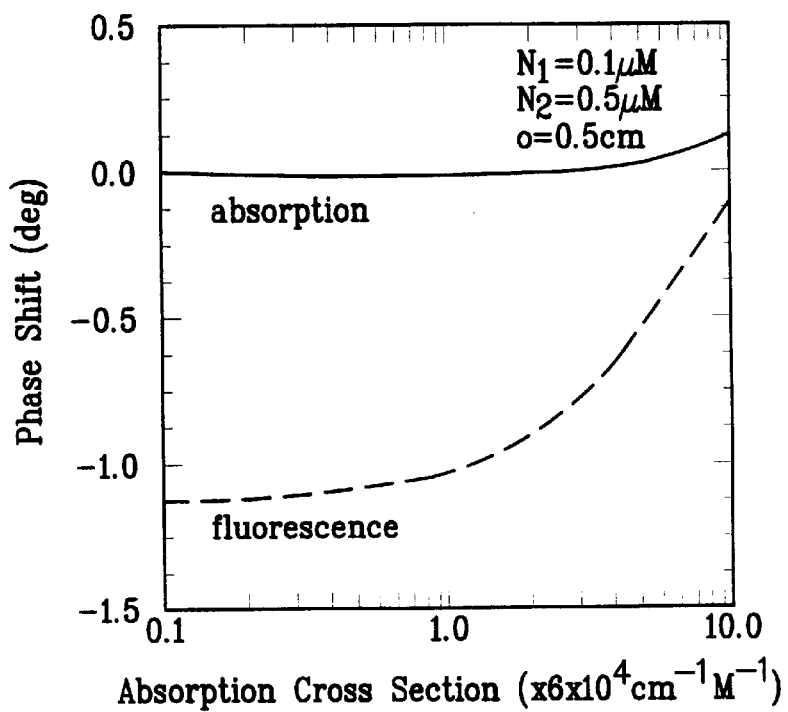

C. Comparison of Absorption and Fluorescence Sensitivities of Fluorophores in Heterogeneous Media Fluorophores increase the local absorption coefficient by an amount $\sigma N_t$ as discussed in Section 2. In a turbid system, and in the presence of a spherical object, the excitation DPDW amplitude [Eqs. (7) and (8)] decreases exponentially as the absorption coefficient of the object increases. An increase in fluorophore absorption cross section ($\sigma$) will thus enhance the total absorption coefficient. As for the fluorescent DPDW, an increase in $\sigma$ introduces two competing effects: The amplitude of the excitation DPDW that is related to the fluorescence source terms (Eq. (16) and (17)) decreases exponentially as $\sigma$ increases; but the fluorescent DPDW amplitude increases linearly as $\sigma$ increases. The phase of the excitation DPDW and fluorescent DPDW always increases when $\sigma$ increases. Our calculations of the normalized amplitude and phase shift of the excitation and fluorescent DPDW's versus fluorophore absorption cross section are shown in FIGS. 15A and 15B. Here, we use the parameters (except the absorption cross section $\sigma$) given in Table 1. The fluorophore concentration contrasts in $N_1/N_2=5$, and the object radius is 0.5. cm. Fluorophore lifetimes inside and outside of the object are taken to be equal (1 ns). The normalized amplitude for the excitation DPDW is $|\phi_1/_{10}|$, and the phase shift is the phase difference between these two DPDW's [see Eqs. (7) and (6)]. The normalized amplitude and phase shift for the fluorescent DPDW are the same as in Subsection 3.B. We find that for smaller fluorophore absorption cross sections, e.g., $\sigma \leq 6\times10^4$ $cm^{-1}M^{-1}$, the fluorescent DPDW gives a better sensitivity for bigger fluorophore absorption cross sections, e.g., a $\sigma \geq 6\times10^4$ $cm^{-1}M^{-1}$.

In the discussion above, we assumed that the noise levels for the excitation DPDW and the fluorescent DPDW are comparable (e.g., 1% amplitude noise and 0.5° phase noise) and that the noise is mainly due to such factors as the source and detector positional errors rather than the shot noise. For a 0.1-m W light source the excitation DPDW fluence rate is $\sim10^{11}$ photons/($cm^2$ s) at the detector for a 6-cm source-detector separation in a homogeneous medium or in a heterogeneous medium with an object of $\sim$0.5-cm radius centered between the source and the detector. The fluorescent DPDW fluence rate in this case is lower than the excitation DPDW fluence rate by $\sim$2-3 orders of magnitude when reasonable concentrations and fluorophore absorption cross sections are used, e.g., $\sigma N_t \sim \mu_a^c$. Even with the loss of 2 orders of magnitude of photon-fluence rate resulting from the detection area and the optical coupling, we find that our detection of heterogeneities is still not shot noise limited in either case.

Theory: The Reverse Problem

As can be seen from above, the propagation of photons through a highly scattering medium with low absorption is well described by the diffusion equation. In this case an amplitude-modulated point source of photons introduced into a diffusive medium produces a DPDW. The wave number k of the DPDW is a function of the medium absorption coefficient $\mu_a$, reduced scattering coefficient $\mu'_s$, and the source modulation frequency $f$. $\mu_a$ and $\mu'_s$ depend on optical wavelength. In a homogeneous infinite medium the spatial part of the DPDW at a position r generated by a point source of amplitude A (in units of photons per second) located at the origin is $U_0(r, k) = A \exp(ikr)/4\pi Dr$ and $k^2=(-v\mu_a+iw)/D$. Here $D=v/(3\mu'_s)$ is the photon diffusion coefficient and v is the speed of light in the medium. $\omega=2\pi f$ is the angular modulation frequency of the source. If a localized fluorophore with volume $d^3r$ and with lifetime $\tau$ is embedded within this medium at position r, the fluorescent photon density $\delta u_{fl}$ measured at a detector position $r_d$ for a source at $r_s$ is $$\delta u_{fl}(r, r_s, r_d) = U_0(r_s - r, k^{\lambda 1})\frac{\eta(r)}{1 - i\omega\tau(r)}\frac{v}{D^{\lambda 2}} \times \quad (29)$$

$$G(r_d - r, k^{\lambda 2})d^3r.$$

Here the wave number $k^{\lambda 1}$ ($k^{\lambda 2}$) depends on the optical properties of the medium at the excitation (fluorescent) wavelength $\lambda 1$ ($\lambda 2$). Equation (29) has three pieces: $U_0(r, k^{\lambda 1})$ represents the demodulation and phase shift that are due to the excitation wave's passage from the source (at $r_s$) to the fluorophore at r, $\eta(r)/[1-i\omega\tau(r)]$ represents the demodulation and phase shift that are due to the strength and lifetime of the fluorophore, and $vG(r_d-r, k^{\lambda 2})/D^{\lambda 2}=v \exp(ik^{\lambda 2}|r_d-r|)/4\pi D^{\lambda 2}|r_d-r|$ represents the demodulation and phase shift that are due to passage of the reradiated wave from r to the detector at $r_d$. $\eta$ is the product of the fluorophore absorption coefficient and fluorescence quantum yield. For a weekly absorbing spatial distribution of fluorophores, the fluorescent photon density wave may be determined by integration over the contributions from all fluorophores:

$$U_{fl}(r_s,r_d) = \int d^3r \delta u_{fl}(r,r_s,r_d). \quad (30)$$

Hereafter we refer to $U_{fl}$ as the fluorescent DPDW. This model is an approximation because $U_0$ and G neglect the effects of heterogeneities on photon propagation from source to fluorophore and from fluorophore to detector. In principle, $U_0$ and G may be updated to include the effects of heterogeneities. The model also assumes that there are no saturation or photon quenching effects.

The fluorescence model in Eq. (30) is of the same form as the first-order perturbation model for a scattering medium with inhomogeneous absorption. Thus it should be feasible to generate images for $\eta(r)$ and $\tau(r)$ by using standard imaging algorithms. (The reconstruction differs from the pure absorption case in that the reconstructed quantity is now complex and is a function of the modulation frequency.) In these reconstruction algorithms we digitize the integral in Eq. (2), [$\eta(r), \tau(r), r \rightarrow \eta_j, \tau_j, r_j$], and for a series of measurements made at source-detector positions $r_{si}, r_{di}$, generate the following matrix equation:

$$U_{fl}(r_{si}, r_{di})_i = \sum_{j=1}^{N_{voxels}} \delta u_{fl}(r_j, r_{si}, r_{di})d^3r_j. \quad (31)$$

This matrix equation can be inverted or solved by many techniques. We have used an algebraic reconstruction method to solve for the real and imaginary parts of the unknown, $\eta_j/(1-i\omega\tau j)$. (The ratio of the imaginary and real parts of the solution yields $\tau$, and then $\eta$ is calculated).

Computer-generated data are obtained from exact solutions to Eq. 32 for the case of a fluorescent sphere in a uniform background. Using forward amplitude and phase data (with added 1% amplitude and 0.1° phase noise), reconstructed images of $\eta$ and $\tau$ are obtained. The measurement geometry is described in FIG. 16A. In the first set of reconstructions all fluorophores are located in the object, and there is no background fluorescence. In FIGS. 16A and 16D, we demonstrate a reconstruction proportional to the fluorophore concentration with source modulation frequencies of 50 and 150 MHz, respectively is shown.

While implementing these reconstructions some isolated voxels have unphysically high values for both $\eta$ and $\tau$. These voxels do not contribute significantly to the total signal since the quantity $\eta/\omega\tau$ is comparable with or smaller than that of the neighboring voxels. As part of the image analysis, these voxels are identified and replaced $\eta$ and $\tau$ with the nearest-neighbor averages. The object size is determined by including any voxel with a fluorophore concentration of at least 50% of the maximum fluorophore concentration. The lifetime reported was the average lifetime of these voxels. FIGS. 16E and 16C (open squares) exhibit good agreement between the average reconstructed value of the lifetime and its known value. Generally, the lifetime reconstructions are more accurate at low source modulation frequencies, for which the occurrence of these spurious voxels is less frequent and the intrinsic phase shift that is due to the lifetime of the fluorophore [$\phi=\tan^{-1}(\omega\tau)$] is far from its saturation value ($\pi/2$).

The image quality is improved if some a priori information is given. For example, if the fluorophore distribution is known, then lifetime-only reconstructions are possible and are shown in FIGS. 16C and 16E(filled circles).

In typical clinical situations there will also be a fluorophore outside the region. In this case, the contributions from inside and outside the heterogeneous region are separated.

$$U_{fl}(r_s, r_d) = \int_{all\,space} dr U_0(r - r_s, k^{\lambda 1}) \times \qquad (32)$$
$$\frac{\eta_0}{1 - i\omega\tau_0} \frac{v}{D^{\lambda 2}} G(r_d - r, k^{\lambda 2}) +$$
$$\int_{heterogeneity} d^3 r \times$$
$$U_0(r - r_s, k^{\lambda 1}) \left[ \frac{\eta(r)}{1 - i\omega\tau(r)} - \frac{\eta_0}{1 - i\omega\tau_0} \right] \times$$
$$\frac{v}{D^{\lambda 2}} G(r_d - r, k^{\lambda 2}).$$

Here $\eta_0$ and $\tau_0$ are the florescence properties outside the heterogeneity and $\eta$ and $\tau$ are the florescence properties inside the heterogeneity. Hereafter, the first term on the right-hand side of Eq. 32 is referred to as $U_{bg}$. If the object contrast is high, i.e., $\eta(r)/[1-i\omega\tau(r)]>\eta_0/(1-i\omega\tau_0)$, then the fluorescent signal that is due to the heterogeneity, $\Delta U_{fl} = U_{fl} - U_{bg}$, is given by $$\Delta U_{fl}(r_s, r_d) = \int d^3 r U_0(r - r_s, k^{\lambda 1}) \times \qquad (33)$$
$$\frac{v\eta(r)}{1 - i\omega\tau(r)} \frac{v}{D^{\lambda 2}} G(r_d - r, k^{\lambda 2}).$$

To accomplish this subtraction, one may use analytic solutions for $U_{bg}$. However, this method requires knowledge of the background lifetime and concentration, which may not be possible in clinical situations. Another option is to eliminate the background signal by subtraction of two measurements having the same source-detector separation, as show in FIG. 17A. In these difference measurements the background (homogeneous) fluorescent contribution will cancel, and only the inhomogeneous part will remain. This method has been employed successfully in absorption reconstructions to reduce the importance of accurate knowledge of the background optical properties. Note that in these images the fluorescent properties of the heterogeneities have been reconstructed; no information about the background fluorescence is derived.

FIG. 17A depicts the scanning geometry used for a system with fluorophore both inside and outside the sphere (radius 0.75 cm). Images of concentration are shown in FIGS. 17B and 17D for source modulation frequencies of 50 and 150 MHz, respectively. The average reconstructed lifetime calculated over the area of the sphere is plotted in FIGS. 17C and 17E for a series of reconstructions on objects with different lifetimes inside the sphere.

Thus, a method has been developed by which the heterogeneous fluorophore distribution and lifetime in a turbid medium may be obtained from tomographic measurements of diffusing photon distributions. The solution for finite systems may be obtained by application of the appropriate boundary conditions.

Therefore, it has been demonstrated that imaging of inhomogeneities in turbid media using DPDW is both possible and practical with the methods and apparatus disclosed and claimed herein. By studying the scattering and distortion of the DPDW by inhomogeneities found therein, the inhomogeneities can be located and their sizes determined for clinical purposes. Alternatively, a fluorescent inhomogeneity can be examined by analyzing the re-radiated DPDW emitted therefrom. In accordance with the invention, it is also possible to combine the dual techniques of examining the refractive, diffractive, scattering, and fluorescent properties of the inhomogeneities to image the objects.

The techniques and apparatus of the present invention provide particularly powerful clinical tools for imaging, locating and sizing tumors in human tissue. Furthermore, the methods and apparatus claimed and disclosed herein should prove to be both economical and efficient imaging tools for clinical diagnosis.

There have thus been described certain preferred embodiments of methods and apparatus for imaging objects using diffuse light provided in accordance with the present invention. While preferred embodiments have been described and disclosed, it will be recognized by those with skill in the art that modifications are within the true spirit and scope of the invention. The appended claims are intended to cover all such modifications.

Appendix A

Basic Relations Used in the Derivation of Analytic Solutions

We have presented analytic solutions for fluorescent diffuse photon density waves in homogeneous turbid media. Using these results and considering a simplified heterogenous system containing a single spherical object, we conclude that approximately fivefold fluorophore concentration contrast and lifetime variation of a factor of 0.2–1.8 provide an observable differential signal to detect an object of 0.5-cm radius centered between the source and the detector with $r_{sd}=6$ cm. This frequency-domain analysis can easily be applied to time-domain experiments by Fourier transformation of the time-domain data. Tomographic image reconstruction techniques can also be used for fluorescence lifetime imaging in turbid media.

$$\int_{4\pi} Y_{lm}(\Omega) Y_{l'm'}^*(\Omega) d\Omega = \delta_{l,l'} \delta_{m,m'}. \tag{A2}$$

The following integral of the product of two Bessel functions is used to perform the radial integration:

$$\int f_1(k_1 r) g_1(k_2 r) r^2 dr = \frac{r^2}{k_1^2 - k_2^2} [k_2 f_1(k_1 r) g_1'(k_2 r) - k_1 f_1'(k_1 r) g_1(k_2 r)], \tag{A3}$$

where $f_1(x)$ and $g_1(y)$ are any spherical Bessel functions of order 1 and $f_1'(x)$ and $g_1'(y)$ are the derivatives of the spherical Bessel function with respect to the x any y argument, respectively.

Appendix B

Definitions of Constants Used in the Analytic Solutions

In solving the heterogenous problem, we obtain several constants of similar functional forms by matching the boundary condition. [Eq. (9)]. They are defined as $$Q_1 = \frac{D_2 k_2 j_1(k_1 a) j_1'(k_2 a) - D_1 k_1 j_1'(k_1 a) j_1(k_2 a)}{D_2 k_2 h_1^{(1)}(k_1 a) j_1'(k_2 a) - D_1 k_1 h_1'^{(1)}(k_1 a) j_1(k_2 a)}, \tag{B1}$$

$$Q_1^f = \frac{D_{2f} k_{2f} j_1(k_{1f} a) j_1'(k_{2f} a) - D_{1f} k_{1f} j_1'(k_{1f} a) j_1(k_{2f} a)}{D_{2f} k_{2f} h_1^{(1)}(k_{1f} a) j_1'(k_{2f} a) - D_{1f} k_{1f} h_1'^{(1)}(k_{1f} a) j_1(k_{2f} a)}, \tag{B2}$$

$$R_1 = \frac{1}{a^2 [D_2 k_2 h_1^{(1)}(k_1 a) j_1'(k_2 a) - D_1 k_1 h_1'^{(1)}(k_1 a) j_1(k_2 a)]}, \tag{B3}$$

$$R_1^f = \frac{1}{a^2 [D_{2f} k_{2f} h_1^{(1)}(k_{1f} a) j_1'(k_{2f} a) - D_{1f} k_{1f} h_1'^{(1)}(k_{1f} a) j_1(k_{2f} a)]}, \tag{B4}$$

$$S_1 = \frac{D_2 k_2 h_1(k_1 a) h_1'^{(1)}(k_2 a) - D_1 k_1 h_1'^{(1)}(k_1 a) h_1^{(1)}(k_2 a)}{D_2 k_2 h_1^{(1)}(k_1 a) j_1'(k_2 a) - D_1 k_1 h_1'^{(1)}(k_1 a) j_1(k_2 a)}, \tag{B5}$$

$$E_1 = \frac{D_{2f} k_{2f} h_1^{(1)}(k_{1f} a) j_1'(k_{2f} a) - D_{1f} k_{1f} h_1'^{(1)}(k_{1f} a) j_1(k_{2f} a)}{D_{2f} k_{2f} h_1^{(1)}(k_{1f} a) j_1'(k_{2f} a) - D_{1f} k_{1f} h_1'^{(1)}(k_{1f} a) j_1(k_{2f} a)}, \tag{B6}$$

$$F_1 = \frac{D_{2f} k_{2f} j_1(k_{1f} a) j_1'(k_{2f} a) - D_{1f} k_{1f} j_1'(k_{1f} a) j_1(k_{2f} a)}{D_{2f} k_{2f} h_1^{(1)}(k_{1f} a) j_1'(k_{2f} a) - D_{1f} k_{1f} h_1'^{(1)}(k_{1f} a) j_1(k_{2f} a)}, \tag{B7}$$

where superscript or subscript f corresponds to the optical properties at fluorescent wavelength $\lambda_{f1}$.

Appendix C

Analytical Solution in a Semi-infinite Homogeneous System

Consider a semi-infinite homogeneous system with a physical boundary at z=0 and a uniform fluorophore distribution in z>0 half-space. For the zero boundary condition, if the real source is at position $$\phi_0^{si}(r', r_s) = \frac{vM_0}{D} \left[ \frac{\exp(ik|r' - r_s|)}{4\pi|r' - r_s|} - \frac{\exp(ik|r' - \underline{r_s}|)}{4\pi|r' - \underline{r_s}|} \right]. \tag{C1}$$

As we have seen in Section 2 [Eq. (4)], the source term for the fluorescent DPDW from the real fluorophore at position r' in z>0 half-space is $$S_f^{real}(r', r_s) = \frac{\sigma N_t}{1 - i\omega\tau} \phi_0^{si}(r', r_s). \tag{C2}$$

Therefore the source term from the corresponding image fluorophore at position $\underline{r}'$ has the same source strength but with a negative sign:

$$S_f^{img}(\underline{r}', r_s) = -S_f^{real}(r', r_s) = -\frac{\sigma N_t}{1 - i\omega\tau} \phi_0^{si}(r', r_s). \tag{C3}$$

The fluorescent DPDW detected at position r generated by the fluorophores at position r' and the image fluorophore at position $\underline{r}'$ around volume element dr' is $$\delta\phi_{0f}^{si-z.b.c.}(r, r', r_s) = \left[ \frac{vS_f^{real}(r', r_s)}{D_f} \frac{\exp(ik_f |r - r'|)}{4\pi|r - r'|} + \frac{vS_f^{img}(\underline{r}', r_s)}{D_f} \frac{\exp(ik_f |r - \underline{r}'|)}{4\pi|r - \underline{r}'|} \right] dr'. \tag{C4}$$

The total fluorescent DPDW can be calculated by integrating Eq. (C4) over z>0 half-space where the real fluorophores are distributed.

$$\delta\phi_{of}^{si-z.b.c.}(r, r_s) = \int_{z'>0} \left[ \frac{vS_f^{real}(r', r_s)}{D_f} \frac{\exp(ik_f |r - r'|)}{4\pi|r - r'|} + \frac{vS_f^{img}(\underline{r}', r_s)}{D_f} \frac{\exp(ik_f |r - \underline{r}'|)}{4\pi|r - \underline{r}'|} \right] dr'$$

$$= \frac{v^2 M_0}{DD_f} \frac{\sigma N_t}{1 - i\omega\tau} \int_{-\infty}^{\infty} dx' dy' \int_0^{\infty} dz' \times$$

$$\left[ \frac{\exp(ik|r' - r_s|)}{4\pi|r' - r_s|} \frac{\exp(ik_f |r - r'|)}{4\pi|r - r'|} - \frac{\exp(ik|r' - \underline{r_s}|)}{4\pi|r' - \underline{r_s}|} \frac{\exp(ik_f |r - r'|)}{4\pi|r - r'|} - \frac{\exp(ik|r' - r_s|)}{4\pi|r' - r_s|} \frac{\exp(ik_f |r - \underline{r}'|)}{4\pi|r - \underline{r}'|} + \frac{\exp(ik|r' - \underline{r_s}|)}{4\pi|r' - \underline{r_s}|} \frac{\exp(ik_f |r - \underline{r}'|)}{4\pi|r - \underline{r}'|} \right]. \tag{C5}$$

When the variable is changed, e.g., z'=−z', the fourth term in Eq. (C5) turns out to be $$\frac{v^2 M_0}{DD_f} \frac{\sigma N_t}{1 - i\omega\tau} \int_{-\infty}^{\infty} dx' dy' \int_{-\infty}^{0} dz' \times \frac{\exp(ik|r' - r_s|)}{4\pi|r' - r_s|} \frac{\exp(ik_f |r - r'|)}{4\pi|r - r'|}$$

We can combine the first and fourth terms and obtain an integral similar to Eq. (5):

$$(1) + (4) = \frac{v^2 M_0}{DD_f} \frac{\sigma N_t}{1 - i\omega\tau} \int_{-\infty}^{\infty} dr' \frac{\exp(ik|r' - r_s|)}{4\pi|r' - r_s|} \times \frac{\exp(ik_f |r - r'|)}{4\pi|r - r'|} \tag{C6}$$

-continued $$= \phi_{0f}(r, r_s).$$

The combination of the second and the third terms gives $$(2) + (3) = -\frac{v^2 M_0}{DD_f} \frac{\sigma N_t}{1 - i\omega\tau} \int_{-\infty}^{\infty} dr' \frac{\exp(ik|r' - r_s|)}{4\pi|r' - r_s|} \times \quad (C7)$$

$$\frac{\exp(ik_f|r - r'|)}{4\pi|r - r'|}$$

$$= \phi_{0f}(r, \underline{r}_s).$$

Finally the fluorescent DPDW in a semi-infinite homogeneous system in which zero boundary conditions are used is $$\phi_{0f}^{si-z.b.c.}(\underline{r},\underline{r}_s) = \phi_{0f}(\underline{r},\underline{r}_s) - \phi_{0f}(\underline{r},\underline{r}_s), \quad (C8)$$

where $\phi_{0f}(r, \underline{r}_s)$ are of the form of Eq. (6).

What is claimed is:

1. A system for imaging fluorophores in a turbid medium comprising:
    an illumination source that illuminates the fluorophores with diffuse photon density waves of a first specified wavelength, thus causing the fluorophores to fluoresce re-radiated diffuse photon density waves of a second wavelength after being illuminated with the diffuse photon density waves of the first specified wavelength;
    a detector that detects the re-radiated diffuse photon density waves of the second wavelength, wherein there is a phase shift between the diffuse photon density waves of the first wavelength and the diffuse photon density waves of the second wavelength; and
    a processor interfaced with the detector that processes data corresponding to the phase shift and the amplitude of the re-radiated waves to determine concentration and lifetime of the fluorophores as a function of spatial position in the turbid medium.

2. The system recited in claim 1 wherein the illumination source comprises at least one laser oriented around the fluorophores which irradiates the fluorophores with the diffuse photon density waves of the first wavelength to cause the fluorophores to fluoresce at the second wavelength.

3. The system recited in claim 2 wherein the detector comprises an optical fiber that is placed in proximity to the fluorophores and a photomultiplier tube interfaced to the optical fiber.

4. The system recited in claim 3 further comprising a switch interfaced with the laser that alternately and sequentially turns on and off the laser, and a radio frequency driver interfaced through the switch with the laser that drives the laser to produce the diffuse photon density waves of the first wavelength.

5. The system recited in claim 4 further comprising a display interfaced with the processor that displays the image of the fluorophores' concentration and lifetime produced by the processor.

6. The system recited in claim 1 wherein the illumination source comprises at least one light emitting diode oriented around the fluorophores which irradiates the fluorophores with the diffuse photon density waves of the first wavelength to cause the fluorophores to fluoresce at the second wavelength.

7. The system recited in claim 1 comprising two illumination sources located symmetrically about the detector.

8. The system recited in claim 1 comprising two detectors located symmetrically about the illumination source.

9. The system recited in claim 1 further comprising means for initially providing information about the position and lifetime of the fluorophores in the turbid medium and wherein the processor is adapted to process the data to further characterize the fluorophores in the turbid medium, wherein the process applies an analytic forward solution.

10. The system recited in claim 1 wherein the processor processes the data to determine at least the position and lifetime of the fluorophore in the turbid medium, wherein the processor further applies a perturbative inverse processing procedure.

11. A method imaging a fluorophores in a turbid medium comprising the steps of:
    illuminating the fluorophores with diffuse photon density waves of a first specified wavelength;
    allowing the fluorophores to fluoresce, thereby re-radiating a diffuse photon density wave having a second wavelength and an amplitude;
    detecting the re-radiated diffuse photon density wave having the second wavelength and amplitude wherein there is a phase shift between the diffuse photon density wave of the first wavelength and the diffuse photon density wave of the second wavelength; and
    analyzing the phase difference and the amplitude to determine concentration and lifetime of the fluorophores as a function of spatial position in the turbid medium.

12. The method recited in claim 11 wherein the illuminating step comprises the step of alternately irradiating the fluorophores with at least two sources of diffuse photon density waves of the first wavelength to cause the fluorophores to fluoresce.

13. The method recited in claim 11 wherein the illuminating step comprises the step of illuminating the fluorophores with at least one laser.

14. The method recited in claim 11 wherein the illuminating step comprises the step of illuminating the fluorophores with at least one light-emitting diode.

15. The method recited in claim 11 further comprising the step of initially providing information about the position of the fluorophores in the turbid medium, and the analyzing step further characterizes the fluorophores in the turbid medium.

16. The method recited in claim 11 wherein the analyzing step determines at least the position of the fluorophores in the turbid medium.

* * * * *

UNITED STATES PATENT AND TRADEMARK OFFICE
CERTIFICATE OF CORRECTION

PATENT NO. : 6,304,771 B1
DATED : October 16, 2001
INVENTOR(S) : Yodh et al.

It is certified that error appears in the above-identified patent and that said Letters Patent is hereby corrected as shown below:

Title page,
Under Related U.S. Application Data, please insert the following paragraph:
"This application is a continuation-in-part of U.S. application Ser. No. 08/637,645, filed Jul. 25, 1996, issued Jun. 29, 1999 as U.S. Pat. No. 5,917,190, which was the National Stage of International Application No. PCT/US94/12486, filed Oct. 31, 1994, which claims priority from U.S. application Ser. No. 08/145,466, filed Oct. 29, 1993."

Column 1,
Line 5, please delete the following paragraph, "This application is a continuation-in-part of U.S. application Ser. No. 08/637,645, filed Jul. 25, 1996, issued Jun. 29, 1999 as U.S. Pat. No. 5,917,190, which was the National Stage of International Application No. PCT/US94/12486, filed Oct. 31, 1994, which claims priority from U.S. application Ser. NO. 08/145,466, filed Oct. 29, 1993."

Column 2,
Line 66, please delete "means"

Column 16,
Line 32, please delete:

$$\phi_{1f} = \int_{Inside} \delta\phi_{1f}(r, r_2, r_s)$$

$$= M_0 v^2 \frac{\sigma N_2}{1 - i\omega\tau_2} \frac{a^2}{k_2^2 - k_{2f}^2} \times \sum_{lm} \{[k_{2f} j_1(k_2 a) j'_1(k'_{2f} a) -$$

$$k_2 j'_1(k_2 a) \times j_1(k_{2f} a)] R_1 R_1^f h_1^{(1)}(k_{1f} r) h_1^{(1)}(k_1 r_s) \times$$

$$Y_{lm}(\Omega) Y_{lm}*(\Omega_s)\}. \qquad (20)$$

and insert the following:

$$\phi_{1f}(r, r_s) = \int_{Inside} \delta\phi_{1f}(r, r_2, r_s)$$

$$= M_0 v^2 \frac{\sigma N_2}{1 - i\omega\tau_2} \frac{a^2}{k_2^2 - k_{2f}^2}$$

$$\times \sum_{lm} \{[k_{2f} j_1(k_2 a) j_1/(k_{2f} a) - k_2 j_1/(k_2 a)$$

$$\times j_1(k_{2f} a)] R_1 R_1^f h_1^{(1)}(k_{1f} r) h_1^{(1)}(k_1 r_s)$$

$$\times Y_{lm}(\Omega) Y_{lm}*(\Omega_s)\}, \qquad (20)$$

UNITED STATES PATENT AND TRADEMARK OFFICE
CERTIFICATE OF CORRECTION

PATENT NO. : 6,304,771 B1
DATED : October 16, 2001
INVENTOR(S) : Yodh et al.

It is certified that error appears in the above-identified patent and that said Letters Patent is hereby corrected as shown below:

Column 20,
Line 17, please delete the following table:

TABLE 1

| Chromophore Optical Properties at $\lambda_{ex}$ and $\lambda_{sr}$ and Other Parameters[o] | | | | | | | | | | |
|---|---|---|---|---|---|---|---|---|---|---|
| $\mu_{a1}^c$ | $\mu_{s1}'$ | $\mu_{a2}^c$ | $\mu_{s2}'$ | $\mu_{o1f}^c$ | $\mu_{s1f}'$ | $\mu_{o2n}^c$ | $\mu_{s2f}'$ | $\sigma$ (cm$^{-1}$M$^{-1}$) | $f$ (MHz) | $r_{sd}$ (cm) |
| 0.02 | 8.0 | 0.04 | 10.0 | 0.025 | 8.0 | 0.05 | 10.0 | $6 \times 10^4$ | 200 | 6 |

[o]The optical properties are in units of cm$^{-1}$; $r_{sd}$ is the source-detector separation.

and insert the following:

TABLE 1

Table 1. Chromophore Optical Properties at $\lambda_{ex}$ and $\lambda_{fl}$ and Other Parameters*

| $\mu_{a1}^c$ | $\mu_{a1}'$ | $\mu_{a2}^c$ | $\mu_{a2}'$ | $\mu_{a1f}^c$ | $\mu_{a1f}'$ | $\mu_{a2f}^c$ | $\mu_{a2f}'$ | $\sigma$ (cm$^{-1}$ M$^{-1}$) | $f$ (MHz) | $r_{sd}$ (cm) |
|---|---|---|---|---|---|---|---|---|---|---|
| 0.02 | 8.0 | 0.04 | 10.0 | 0.025 | 8.0 | 0.05 | 10.0 | $6 \times 10^4$ | 200 | 6 |

*The optical properties are in units of cm$^{-1}$; $r_{sd}$ is the source-detector separation.

Signed and Sealed this

Fourth Day of June, 2002

Attest:

Attesting Officer

JAMES E. ROGAN
Director of the United States Patent and Trademark Office